(12) United States Patent
Mutharasan et al.

(10) Patent No.: US 8,809,065 B2
(45) Date of Patent: Aug. 19, 2014

(54) DETECTION AND MEASUREMENT OF MASS CHANGE USING AN ELECTROMECHANICAL RESONATOR

(75) Inventors: Rajakkannu Mutharasan, West Chester, PA (US); Sen Xu, Philadelphia, PA (US); Blake N. Johnson, Philadelphia, PA (US); Harsh Sharma, Philadelphia, PA (US); Ramji S. Lakshmanan, Philadelphia, PA (US)

(73) Assignee: Drexel University, Philadelphia, PA (US)

( * ) Notice: Subject to any disclaimer, the term of this patent is extended or adjusted under 35 U.S.C. 154(b) by 547 days.

(21) Appl. No.: 12/783,373

(22) Filed: May 19, 2010

(65) Prior Publication Data

US 2010/0297687 A1    Nov. 25, 2010

Related U.S. Application Data

(60) Provisional application No. 61/216,573, filed on May 19, 2009.

(51) Int. Cl.
  *G01N 29/22* (2006.01)
(52) U.S. Cl.
  CPC .................................. *G01N 29/22* (2013.01)
  USPC ............................. 436/149; 73/579; 73/61.75
(58) Field of Classification Search
  CPC .................................................. G01N 29/022
  USPC ................................................. 73/579, 61, 75
  See application file for complete search history.

(56) References Cited

U.S. PATENT DOCUMENTS 5,883,705 A    3/1999    Minne et al.

FOREIGN PATENT DOCUMENTS

| JP | 6-131711 A | 5/1994 |
|---|---|---|
| KR | 10-0613398 B1 | 8/2006 |
| WO | WO 2007/087328 A2 | 8/2007 |

OTHER PUBLICATIONS

Campbell, G. A. et al. Detection of *Staphylococcus enterotoxin* B at picogram levels using piezoelectric-excited millimeter-sized cantilever sensors, Sensors ans Actuators B, 2007, vol. 126, pp. 354-360.*
PCT Application No. PCT/US2010/035422 : International Search Report and Written Opinion of the International Searching Authority, May 19, 2010, 9 pages.

* cited by examiner

*Primary Examiner* — Robert Xu
(74) *Attorney, Agent, or Firm* — Baker & Hostetler LLP

(57) ABSTRACT

A change in impedance of a electromechanical resonating sensor is utilized to detect and/or measure a change in mass accumulated on the sensor. The impedance is monitored at a fixed frequency. The fixed frequency may be at or near the resonance frequency of the sensor. In various configurations, the sensor comprises a quartz crystal microbalance sensor or a piezoelectric cantilever sensor.

12 Claims, 40 Drawing Sheets

TABLE 1

| Sensor No. | $f_R$ (kHz) $\|Z\|$ | Q-value | α (kHz) | vs. f in $(f_R - α) \leq f \leq (f_R + α)$ | $R^2$ |
|---|---|---|---|---|---|
| Sensor 1 | 925.50 | 40 ± 1 | 10.50 | = 31.761$f$ - 28954 | 0.974 |
| Sensor 2 | 909.00 | 43 ± 1 | 11.50 | = 29.004$f$ - 25948 | 0.962 |
| Sensor 3 | 912.00 | 38 ± 1 | 11.75 | = 23.956$f$ - 21436 | 0.961 |
| Sensor 4 | 876.00 | 42 ± 1 | 10.50 | = 37.132$f$ - 32080 | 0.960 |
| Sensor 5 | 877.00 | 35 ± 1 | 12.00 | = 22.312$f$ - 19111 | 0.984 |
| Sensor 6 | 910.00 | 45 ± 1 | 10.00 | = 34.955$f$ - 31431 | 0.977 |
| Sensor 7 | 911.00 | 60 ± 1 | 8.00 | = 16.157$f$ - 14373 | 0.983 |

FIGURE 3

DETECTION AND MEASUREMENT OF MASS CHANGE USING AN ELECTROMECHANICAL RESONATOR

STATEMENT OF FEDERALLY SPONSORED RESEARCH

Portions of the herein disclosure have been supported in part by a grant from an Environmental Protection Agency STAR Grant R833007. The government has certain rights in the invention.

CROSS REFERENCE TO RELATED APPLICATIONS

The present application claims priority to U.S. Provisional Patent Application No. 61/216,573, entitled "A Novel Method For Monitoring Mass-Change Response Of Piezoelectric Excited Millimeter-Sized Cantilever (PEMC) Sensors," filed May 19, 2009 which is hereby incorporated by reference in its entirety.

TECHNICAL FIELD

The technical field generally relates to detecting and/or measuring a change in mass, and more specifically relates to detecting and/or measuring a change in mass via a detected and/or measure change in impedance of an electromechanical resonator.

BACKGROUND

Electromechanical resonating sensors can be utilized to detect a wide range of analytes (substance under analysis). However, detection and/or measurement using an electromechanical resonating sensor typically require complex measurement and data management, measurements at the resonance frequency of the sensor, and/or characterization of the sensor at resonance frequency. Example electromechanical resonating sensors include Quartz Crystal Microbalance (QCM) sensors, piezoelectric cantilever sensors, or the like. For QCM sensors, motional resistance and other circuit parameters at a resonance frequency of the QCM sensor can be used to detect an analyte accumulated on the QCM sensor. Cantilever sensors can be utilized in both static (bending) mode and dynamic (resonance) mode. Static mode sensors bend in proportion to surface stress caused by surface binding. In static mode, the deformation of the cantilever arm is measured to determine if an analyte is present. Dynamic mode sensors exhibit resonant frequency decrease as a result of mass-change due to analyte binding. In dynamic mode, a resonance frequency is measured to determine if an analyte is present. The complexity and data management associated with detection and/or measurement using an electromechanical resonating sensor becomes even worse if multiple sensors are to be monitored.

SUMMARY

Impedance of an electromechanical resonating sensor is utilized to detect and/or measure a change in mass accumulated on the sensor. In an example embodiment, impedance is monitored at a fixed frequency. In another example embodiment, the fixed frequency is at or near the resonance frequency of the piezoelectric cantilever sensor. Example electromechanical resonating sensors include Quartz Crystal Microbalance (QCM) sensors and piezoelectric cantilever sensors. In an example configuration, a piezoelectric cantilever includes a piezoelectric layer and a non-piezoelectric layer attached to the piezoelectric layer such that a distal end of the non-piezoelectric layer extends beyond a distal end of the piezoelectric layer or a distal end of the piezoelectric layer extends beyond a distal end of the non-piezoelectric layer. That is, the piezoelectric layer is coupled to the non-piezoelectric layer such that the piezoelectric layer and the non-piezoelectric layer are not coextensive. In various configurations of the piezoelectric cantilever sensor, the piezoelectric layer, the non-piezoelectric layer, or both are anchored to at least one base. Electrodes are operatively associated with the piezoelectric layer. The piezoelectric cantilever sensor is utilized to sense mass change.

BRIEF DESCRIPTION OF THE DRAWINGS

The foregoing summary, as well as the following detailed description, may be better understood when read in conjunction with the appended drawings. For the purpose of illustrating detection and measurement of mass change using a piezoelectric cantilever sensor, exemplary drawings are shown, however, detection and measurement of mass change using a piezoelectric cantilever sensor are not limited to the specific methods and instrumentalities illustrated.

FIG. 3 illustrates a table showing impedance vs. excitation frequency for example piezoelectric cantilever sensors.

DETAILED DESCRIPTION OF ILLUSTRATIVE EMBODIMENTS

Figure 1:
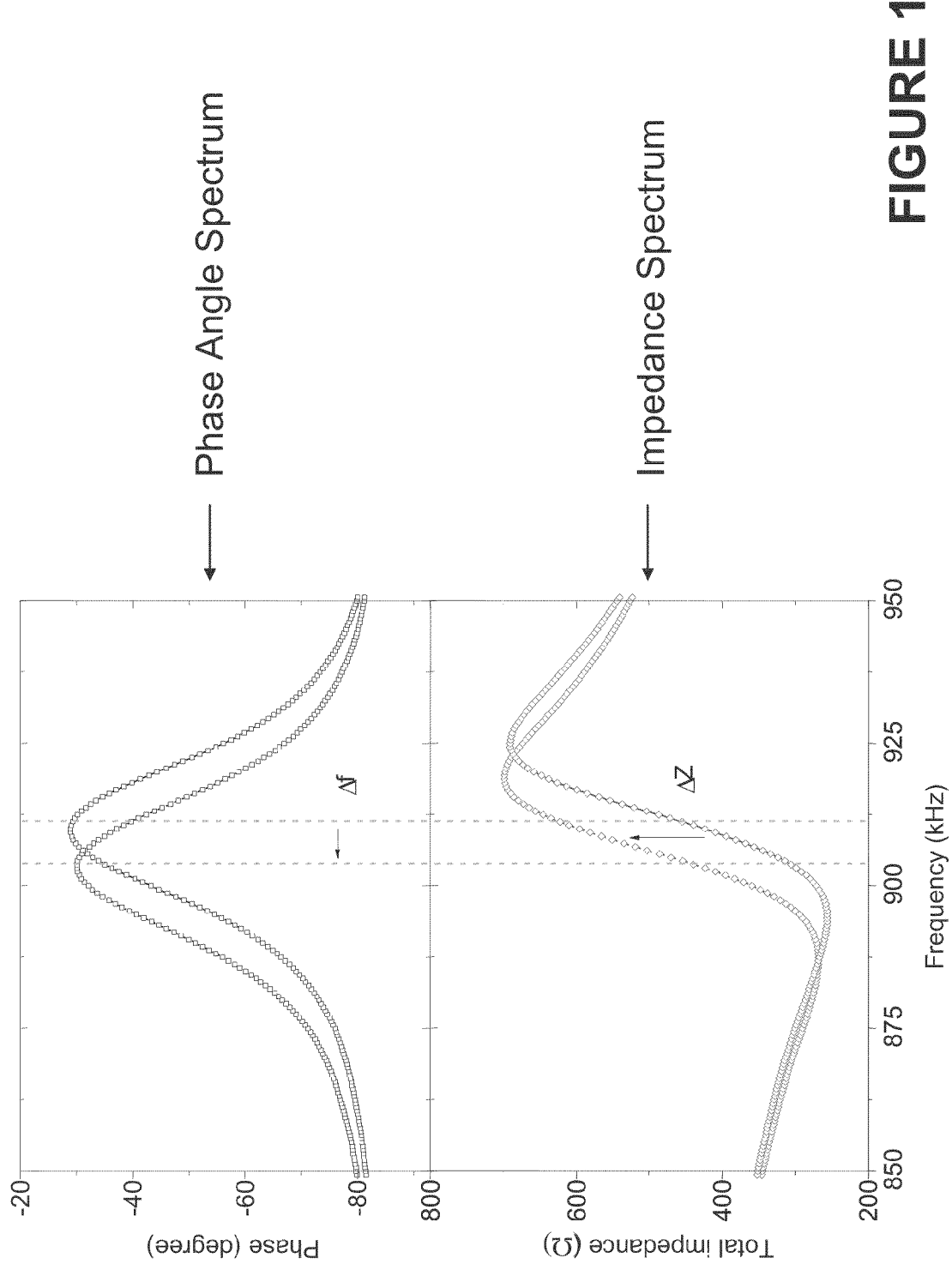
FIG. 1 illustrates a phase angle spectrum and an impedance spectrum for an example piezoelectric cantilever sensor.

Detection and/or measurement of a change in mass accumulated on an electromechanical resonating sensor is/are accomplished via monitoring impedance of the electromechanical resonating sensor. Measurement of total impedance ($|Z(f)|$) at a fixed (constant) frequency is described herein. The fixed frequency can be any appropriate frequency. For example the frequency can be a resonance frequency, ($f_R$), of the electromechanical resonating sensor. The fixed frequency can be other than a resonance frequency of the electromechanical resonating sensor. The fixed frequency can be a frequency with a predetermined tolerance (e.g., +/−1 kHz) of the resonance frequency. The herein described impedance approach can be implemented in a relatively short amount of time using a relatively simple measurement system. As such, the herein described impedance approach lends itself to a simplified implementation for a single piezoelectric cantilever sensor as well as for high throughput applications involving a large numbers of piezoelectric cantilever sensors.

Applications and experiments involving the herein described impedance approach are described with respect to a piezoelectric cantilever sensor. However, it is to be understood that application of the herein described impedance is not limited thereto. The herein described impedance approach is applicable to any appropriate sensor or measuring device or mechanism. For example the herein described impedance approach is applicable to electromechanical resonating sensors, QCM sensors, piezoelectric cantilever sensors, or the like.

It is shown, experimentally, that the total impedance change at a fixed frequency directly relates to resonance frequency shifts of a piezoelectric cantilever sensor. This is associated with two properties: (1) Q-value of piezoelectric cantilever sensors is in the range of 30 to 60, (2) in a typical biosensing experiment, the change in resonance frequency is less than 5 kHz. Two sensing experiments are described herein. In the first experiment, mass-change response due to density is evaluated. In the second experiment, samples containing the pathogen *E. coli* O157:H7 are exposed to an antibody-functionalized piezoelectric cantilever sensor and the resulting response of impedance is shown to be the detection response.

An example configuration of a piezoelectric cantilever sensor comprises a two layer composite structure of non-uniform thickness comprising a piezoelectric material (e.g., lead zirconate titanate, PZT) layer and a glass layer, for example. The PZT layer acts as an actuating and sensing element, while the glass layer provides a surface for antibody, nucleic acid immobilizations, or the like. Piezoelectric cantilever sensors are described in detail later in the herein specification.

In an example configuration, the resonance frequency of a uniform cross section cantilever in an inviscid fluid is given by Equation (1).

$$\frac{f_{R_{fluid}}}{f_{R_{vac}}} = \left(1 + \frac{\pi \rho b}{4\rho_c h}\right)^{-1/2} \quad (1)$$

where $f_{R_{fluid}}$ and $f_{R_{vac}}$ are the resonance frequencies in fluid and vacuum respectively, $\rho_c$ is the density of the cantilever, b and h are the width and thickness of the cantilever, and $\rho$ is the density of the surrounding fluid. The implied assumptions in equation (1) are: (1) uniform cross section, (2) cantilever length is much longer than its thickness, and (3) amplitude of vibration is much smaller than any sensor length scale. For the case of a piezoelectric cantilever sensor, using approximations, the ratio of resonant frequency in aqueous solutions of various densities to that in water is given by Equation (2).

$$\frac{f_{Rw}}{f_{Rx}} = \frac{\sqrt{1+\gamma\rho_x}}{\sqrt{1+\gamma\rho_w}} \quad (2)$$

where $\gamma$ is a sensor parameter that accounts for non-uniform thickness of a piezoelectric cantilever sensor. The terms $f_{Rw}$ and $f_{Rx}$ refer to resonance frequencies in water and in solution of solute mass fraction X, respectively. An example value of $\gamma$ is ~2. Equation (2) suggests that as liquid density increases, the resonance frequency of a piezoelectric cantilever sensor decreases, and vice versa.

FIG. 1 illustrates a phase angle spectrum and an impedance spectrum for an example piezoelectric cantilever sensor. The phase angle represents the vectorial difference between excitation voltage and the resulting current signal measured at steady state by an impedance analyzer. The impedance of the sensor is also shown as a function of the excitation frequency. As depicted in FIG. 1, the example piezoelectric cantilever sensor exhibits resonance near 912 kHz with a Q-value of 38. The impedance rises linearly from 250Ω at 900 kHz to 700Ω at 925 kHz. As depicted in FIG. 1, the impedance is a linear function of frequency in the region described by, $(f_R-\alpha) \le f \le (f_R+\alpha)$, where $\alpha$ is ~12 kHz. In an example detection experiment, the change in resonant frequency associated with detection may be a few kHz. For example, binding of antigens such as *E. coli* O157:H7 at 100 cells/mL can cause a frequency decrease of ~1 kHz, while Staphylococcus enterotoxin B (SEB) at 100 fg showed a decrease of ~250 Hz. Thus resonant frequency movement is well within the frequency bound between $(f_R-\alpha)$ and $(f_R+\alpha)$. In the neighborhood of $f_R$, impedance at frequency f can be approximated by Equation (3).

$$|Z(f)| = |Z(f_R)| + \frac{\partial |Z|}{\partial f}\bigg|_{f=f_R}(f-f_R) \quad (3)$$

where the expression $$\frac{\partial |Z|}{\partial f}\bigg|_{f=f_R}$$

gives the slope-dependence of impedance near $f_R$, and f is an arbitrary frequency near resonance frequency. When a change in fluid density or binding of the target analyte causes small changes in resonant frequency, the impedance spectrum in the $(f_R-\alpha) \le f \le (f_R+\alpha)$ region will move in a parallel fashion as illustrated in FIG. 1. Therefore, it is deduced that the measurement of the impedance change at a set frequency is a useful method for monitoring sensor response.

Combining Equations (2) and (3), and defining $|Z(f_{nr})|$ as impedance measured at a fixed non-resonant monitoring frequency ($f_{nr}$), $|Z(f_{nr})|$ can be expressed as a function of fluid density as shown in Equation (4).

$$\frac{f_{Rw}}{f_{Rx}} = \frac{\frac{\partial |Z|}{\partial f}\bigg|_{f=f_{Rx}}}{\frac{\partial |Z|}{\partial f}\bigg|_{f=f_{Rw}}} \left(\frac{|Z(f_R)|_w + \frac{\partial |Z|}{\partial f}\bigg|_{f=f_{Rw}} \cdot f_{nr} - |Z(f_{nr})|_w}{|Z(f_R)|_x + \frac{\partial |Z|}{\partial f}\bigg|_{f=f_{Rx}} \cdot f_{nr} - |Z(f_{nr})|_x}\right) = \frac{\sqrt{1+\gamma\rho_x}}{\sqrt{1+\gamma\rho_w}} \quad (4)$$

where $$\frac{\partial |Z|}{\partial f}\bigg|_{f=f_{Rx}}, \frac{\partial |Z|}{\partial f}\bigg|_{f=f_{Rw}},$$

$|Z(f_R)|_w$, $|Z(f_R)|_x$, $f_{nr}$ are each constant values in the $(f_R-\alpha) \le f \le (f_R+\alpha)$ region.

Simplifying Equation (4) by introducing $$\alpha_x = \frac{\partial |Z|}{\partial f}\bigg|_{f=f_{Rx}}, \alpha_w = \frac{\partial |Z|}{\partial f}\bigg|_{f=f_{Rw}},$$

$$\beta_x = |Z(f_{Rx})| + \frac{\partial |Z|}{\partial f}\bigg|_{f=f_{Rx}} \cdot f_{nr}, \beta_w = |Z(f_{Rw})| + \frac{\partial |Z|}{\partial f}\bigg|_{f=f_{Rw}} \cdot f_{nr},$$

Equation (5) results.

$$\frac{f_{Rw}}{f_{Rx}} = \frac{\alpha_x(\beta_w - |Z(f_{nr})|_w)}{\alpha_w(\beta_x - |Z(f_{nr})|_x)} = \frac{\sqrt{1+\gamma\rho_x}}{\sqrt{1+\gamma\rho_w}} \quad (5)$$

Note that $f_R$ and $|Z(f_{nr})|$ increase when density increases in Equation (5), and vice versa. The above relationship holds true in the $(f_R-\alpha) \le f \le (f_R+\alpha)$ region.

Density Change Experiment to Verify Equation (5)

All chemicals for density experiments were purchased from Sigma-Aldrich. Aqueous solutions of NaCl, glycerol (99%) and 1-propanol (99%) were prepared in de-ionized (DI) water (18 MΩ, Mill-Q system, Millipore) at various mass fractions. Phosphate buffered saline (PBS, 10 mM, pH 7.4) were prepared in DI water. Protein G was purchased from Pierce (Rockford, Ill.). Aliquots of 20 μg/mL solutions were prepared in PBS and stored at −20° C. Goat polyclonal anti-*E. coli* O157:H7 antibody and *E. coli* O157:H7 positive controls were purchased from KPL (Kirkegaard & Perry Laboratories, Gaithersburg, Md.). Aliquots of 20 μg/mL antibody solutions were prepared in PBS and stored at −20° C.; various concentrations of *E. coli* O157:H7 positive controls were prepared in PBS and stored at 4° C.

Piezoelectric Cantilever Sensor Fabrication

Briefly, the piezoelectric cantilever sensor comprised two layers: a PZT layer (Piezo Systems, Woburn, Mass.) and a glass layer (SPI, West Chester, Pa.), bonded by a non-conductive adhesive. The dimensions of the PZT and glass were 2.7×1'0.127 mm, and 2×1×0.160 mm (l×w×t), respectively. The PZT end was anchored at one end and glass layer was attached at the free-end. Wires were soldered to electrodes of PZT layer and epoxy fixed in 6 mm glass tubing, and subsequently the sensor was coated with 10 μm parylene C as per vendor supplied protocol in a parylene coating machine (PDS 2010 LABCOTER® 2, SCS). The parylene coating provides resistance to water and chemicals since all measurements were made in liquids.

Experimental Setup and Methods

The experimental setup comprised an impedance analyzer (Agilent 4294A) and a custom-fabricated apparatus. The flow cell with 120 μL holding volume was maintained at 25.0±0.1° C. in an incubator (Quincy Lab, 10-140E) to ensure constant temperature. Prior to an experiment, the sensor surface was cleaned with 100% ethanol followed by a copious amount of DI water. The entire flow system was rinsed with ethanol, followed by DI water. Total impedance change during an experiment was measured by impedance analyzer with a LabView® program that recorded impedance and phase angle. In a typical experiment, the excitation voltage was 100 mV and monitoring frequency was set at ~1 kHz of resonance.

For density experiments, both batch and flow methods were used. In batch mode, the piezoelectric cantilever sensor was immersed completely in test liquid and the resonant frequency was monitored until steady state was reached. In flow mode, piezoelectric cantilever sensor was installed in a flow cell and DI water flow was set at a flow rate of 0.6 mL/min. After impedance value at the chosen frequency value reached steady value, test solutions were switched into the flow system, and DI water was turned off at the same time. The impedance value was monitored until steady state was reached.

$E.$ $coli$ O157:H7 detection experiments were conducted in the flow apparatus at 25.0° C., and all measurements were carried out similar to the density experiments in flow mode, except that flow rate was 0.8 mL/min. For these experiments, 2 mm$^2$ PEMC sensor tip surface was freshly sputter-coated with 100 nm gold in a Desk IV sputtering system (Denton Vacuum, Moorestown, N.J.). After stabilization in PBS flow, 1 mL Protein G (20 μg/mL) was introduced and the flow was set in recirculation mode. Once immobilization was complete indicated by impedance reaching a stable value, the flow was changed to PBS to rinse the flow circuit. Subsequently 1 mL anti-$E.$ $coli$ O157:H7 (20 μmL) was introduced in a manner similar to Protein G. Binding of anti-$E.$ $coli$ O157:H7 was monitored by impedance response and after steady state was reached, the flow circuit was flushed with PBS and 1 mL $E.$ $coli$ O157:H7 (1,000 cells/mL) was introduced and set to recirculation mode.

Impedance Spectrum of Piezoelectric Cantilever Sensor

Figure 2:
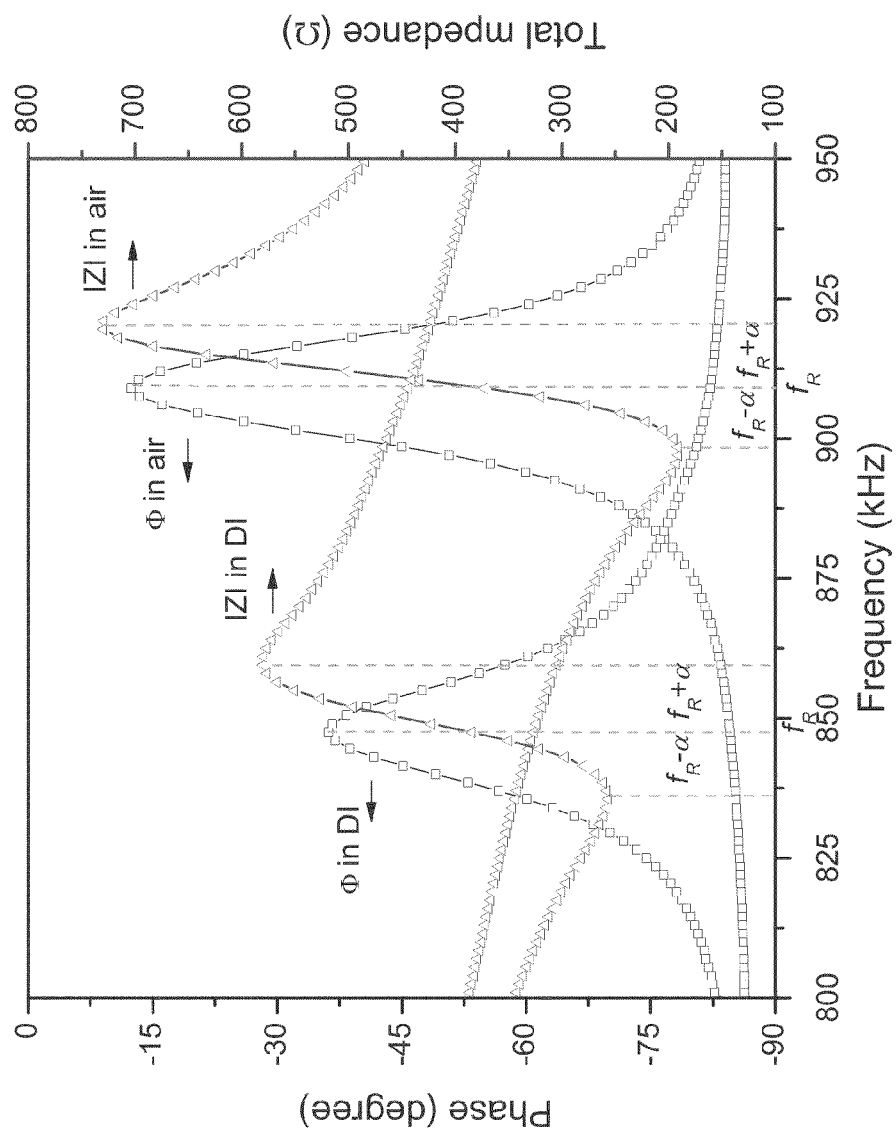
FIG. 2 illustrates example spectra of phase angle and total impedance as a function of excitation frequency in air and in DI water.

FIG. 2 illustrates example spectra of phase angle and total impedance as a function of excitation frequency in air and in DI water (deionized or purified water). The fabricated piezoelectric cantilever sensor exhibited high-mode resonance near 900 kHz with Q-value in the range of 35-60. When the surrounding medium of the sensor was changed from air to DI water, the resonance frequency decreased by ~60 kHz, from 909 kHz to 848 kHz, the phase angle of the resonance peak decreased from −12.4° to −36.2°, and the Q-value decreased from 43 to 33. As shown in FIG. 2, when excitation frequency was increased, the impedance value decreased and reached a minimum, and then increased in a near linear fashion to a maximum, followed by a further decrease. The maximum phase angle occurs midway between the minimum and maximum impedance values.

FIG. 3 illustrates a table, Table 1, showing impedance, (|Z|), vs. excitation frequency, (f), in the region $(f_R-\alpha) \leq f \leq (f_R+\alpha)$ for seven example piezoelectric cantilever sensors. Over 200 piezoelectric cantilever sensors with the same herein described geometric design were characterized, and seven representative ones and their impedance properties are summarized in Table 1. The magnitude of the parameter a depends on Q-value. When Q is in the range of 35~60, α is 8~12 kHz. In many sensing experiments with piezoelectric cantilever sensors, the resonant frequency response was on the order of 0.1 to 5 kHz. Therefore, it is reasonable to conclude that impedance varies linearly with frequency over the frequency range of interest in a similar sensing experiment.

Response of Piezoelectric Cantilever Sensor to Density Change

Having shown that impedance profile of the piezoelectric cantilever sensor is a near-linear function of frequency near resonant frequency, the performance of the two approaches is compared with sensor responses to density change. Diluted aqueous solutions of NaCl, glycerol, and 1-propanol solutions were used as suitable density-test solution for introducing both increase and decrease density changes.

Figure 4:
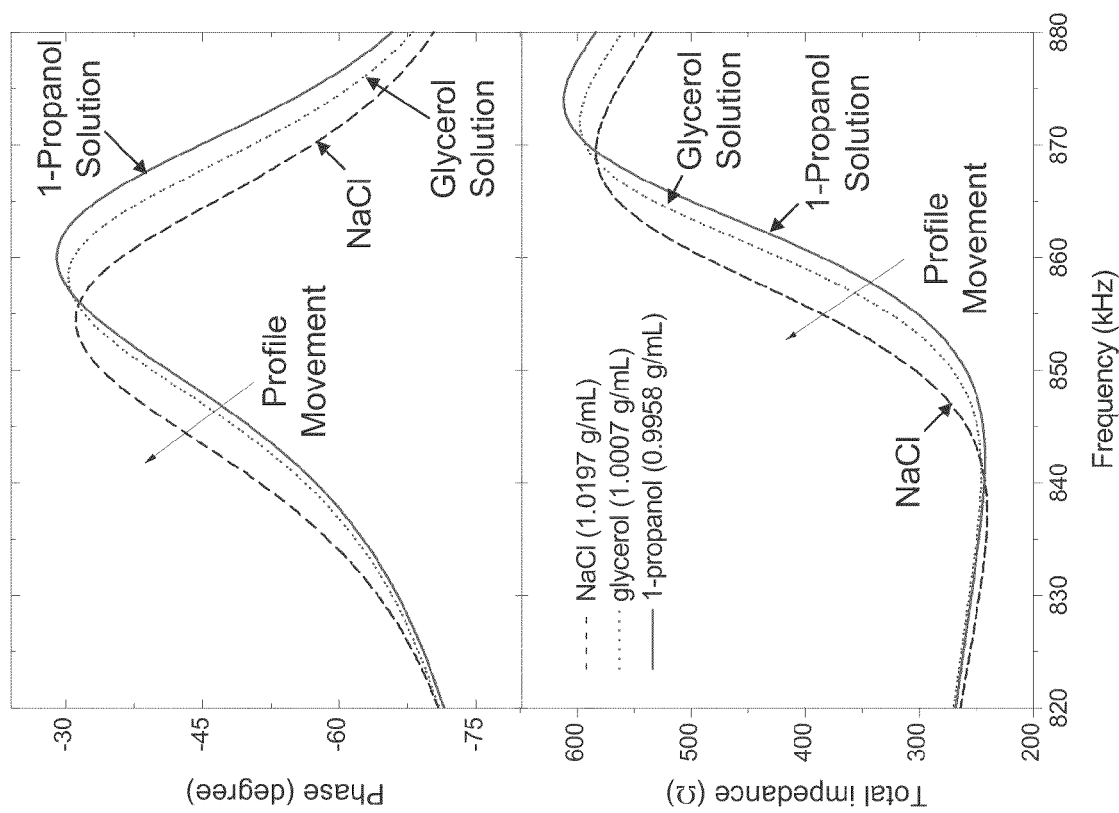
FIG. 4 illustrates the resonance frequency and total impedance responses of a piezoelectric cantilever sensor in liquids of various densities.

FIG. 4 illustrates the resonance frequency and total impedance responses of a piezoelectric cantilever sensor ($f_R$=858 kHz, Q=35) in liquids of various densities. Dashed lines indicate NaCl-solution (X=0.0301, ρ=1.0197 g/mL). Dotted lines are the spectra in glycerol solution (X=0.0107, μ=1.0007 g/ml). Solid lines are the spectra in 1-propanol solution (X=0.0100, ρ=0.9958 g/ml). Note the impedance profile moves to the right in a lower density solution. Initially the sensor was allowed to reach steady state in NaCl-solution (X=0.0301, ρ=1.0197 g/mL). Subsequently, the steady values in glycerol solution (X=0.0107, ρ=1.0007 g/mL) and 1-propanol solution (X=0.0100, ρ=0.9958 g/mL) were recorded. Resonance frequency increased from 855.125 kHz to 858.500 kHz (Δf=3,375 Hz), and then to 860.375 kHz (Δf=1,875 Hz) in the three solutions noted. Phase angle increased from −31.34° to −29.36°, then to −28.98°, respectively. That is, as density decreased from 1.0197 g/mL to 1.0007 g/mL, and then to 0.9958 g/mL, both resonance frequency and the phase angle increased. As shown in FIG. 4, for the three changes, the impedance spectrum moved in the same direction as resonance frequency. Further, the total impedance spectra for the three cases are nearly parallel to each other in the range of 850-865 kHz. Note that the total impedance in higher density solution is larger than it is in lower density liquids; and, the larger the resonance frequency change, the higher the impedance response magnitude. The measurement of impedance change at a fixed frequency gives data directly related to density change of liquids, or effective added mass response. Since the sensor is used for obtaining mass-change response, impedance (|Z|) at a fixed frequency can be monitored rather than a more laborious method of monitoring resonant frequency.

Choice of Monitoring Frequency

Figure 5:
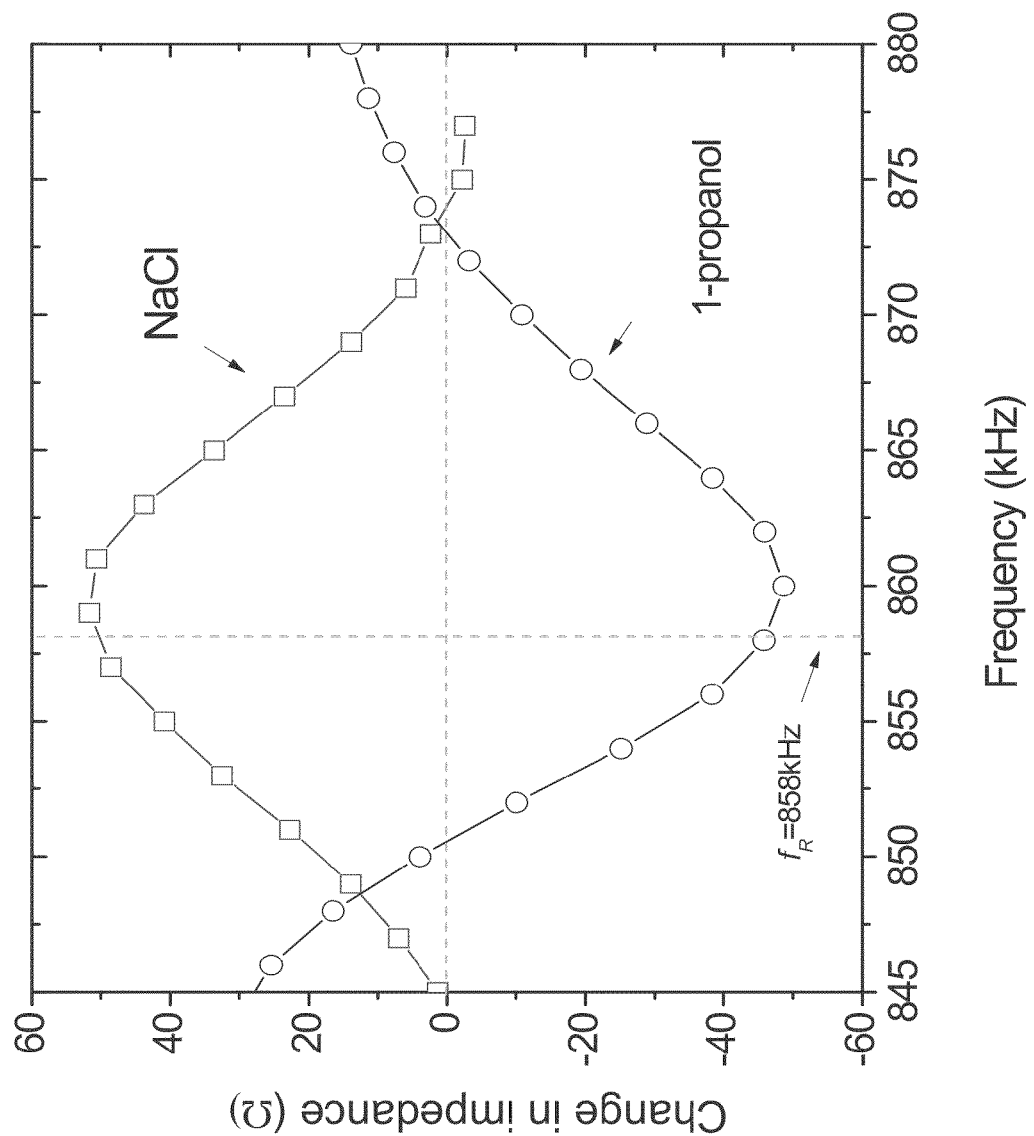
FIG. 5 illustrates total impedance response to density change at various monitoring frequencies near resonance frequency (±20 kHz).

FIG. 5 illustrates total impedance response to density change at various monitoring frequencies near resonance frequency (±20 kHz). The choice of frequency for monitoring total impedance response to density change or biological sensing experiments directly affects sensitivity. Responses in NaCl solution (X=0.0100, ρ=1.0055 g/mL) and 1-propanol solution (X=0.0100, ρ=0.9958 g/mL) were symmetric to each other. The sensor response was examined at various frequencies near $f_R$ for a given imposed change. NaCl-solution (X=0.0100, ρ=1.0055 g/mL) and 1-propanol solution (X=0.0100, ρ=0.9958 g/mL) were used as test solutions, and responses were determined with respect to DI water. In all cases, on both sides of resonance frequency, impedance increased when changing from DI water to NaCl solution, and is consistent with Equation (5). The location where maximum impedance change occurred was at f=859 kHz, which is ~1 kHz higher than the resonance frequency ($f_R$=858 kHz). For NaCl-solution, decrease of the response magnitude occurred as monitoring frequency was either increased or decreased away from the resonance frequency. Beyond the region of +15~–13 kHz from resonance frequency, the impedance value decreased instead of an increase. For 1-propanol solution, the impedance response was exactly in the opposite direction from that for NaCl solution, since 1-propanol solution is less dense than DI water. The features of the impedance response were similar except that response decreased.

Results in FIG. 5 indicate that impedance change is largest in the region close to resonance frequency. Therefore, monitoring frequency within ±2 kHz of the resonance frequency is suitable for total impedance change measurement. The frequency at $f=f_R+1$ kHz was used as it gave nearly the maximum response for the imposed density changes.

Comparison of Impedance Response with Resonant Frequency Response

In order to examine the validity of the impedance monitoring approach to the established method of resonance frequency monitoring, a wide range of aqueous solutions of NaCl, glycerol and 1-propanol of various mass fraction were prepared and both resonant frequency and total impedance changes were measured following changes from DI water to various density solutions ranging from 0.9698 to 1.1087 g/mL. The density of DI water is 0.9985 g/mL (X=0), and density values of various solutions are from reference.

Figure 6:
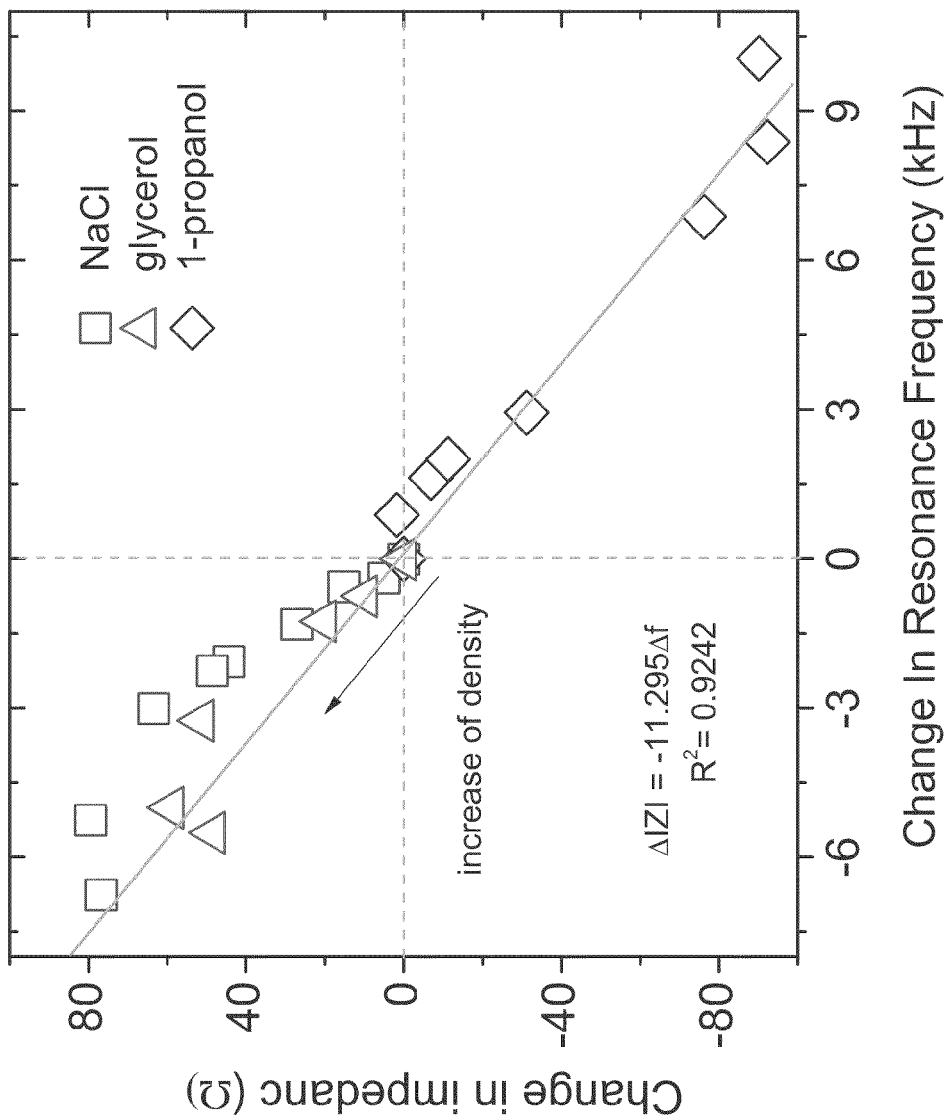
FIG. 6 illustrates resonance frequency and total impedance response to density changes.

FIG. 6 illustrates resonance frequency ($\Delta f$) and total impedance response to density changes from 0.9698 g/mL to 1.1087 g/mL. Total impedance change due to density change at f=859 kHz is plotted as a function of resonant frequency change. When liquid density was increased (or decreased), total impedance at f=859 kHz increased (or decreased), and for the same conditions the resonance frequency decreased (or increased). The higher the density difference, the larger was the resonance frequency and total impedance change. This applied to all three test solutions. From experimental results shown, density differences as low as 0.0001 g/mL are easily measurable using impedance or resonance frequency measurements. The response of total impedance at f=859 kHz and resonance frequency gave excellent correlation ($\Delta |Z|=-11.295\ \Delta f$, $R^2$=0.9242).

Response of Sensor to Density Changes in a Flow Apparatus

Figure 7:
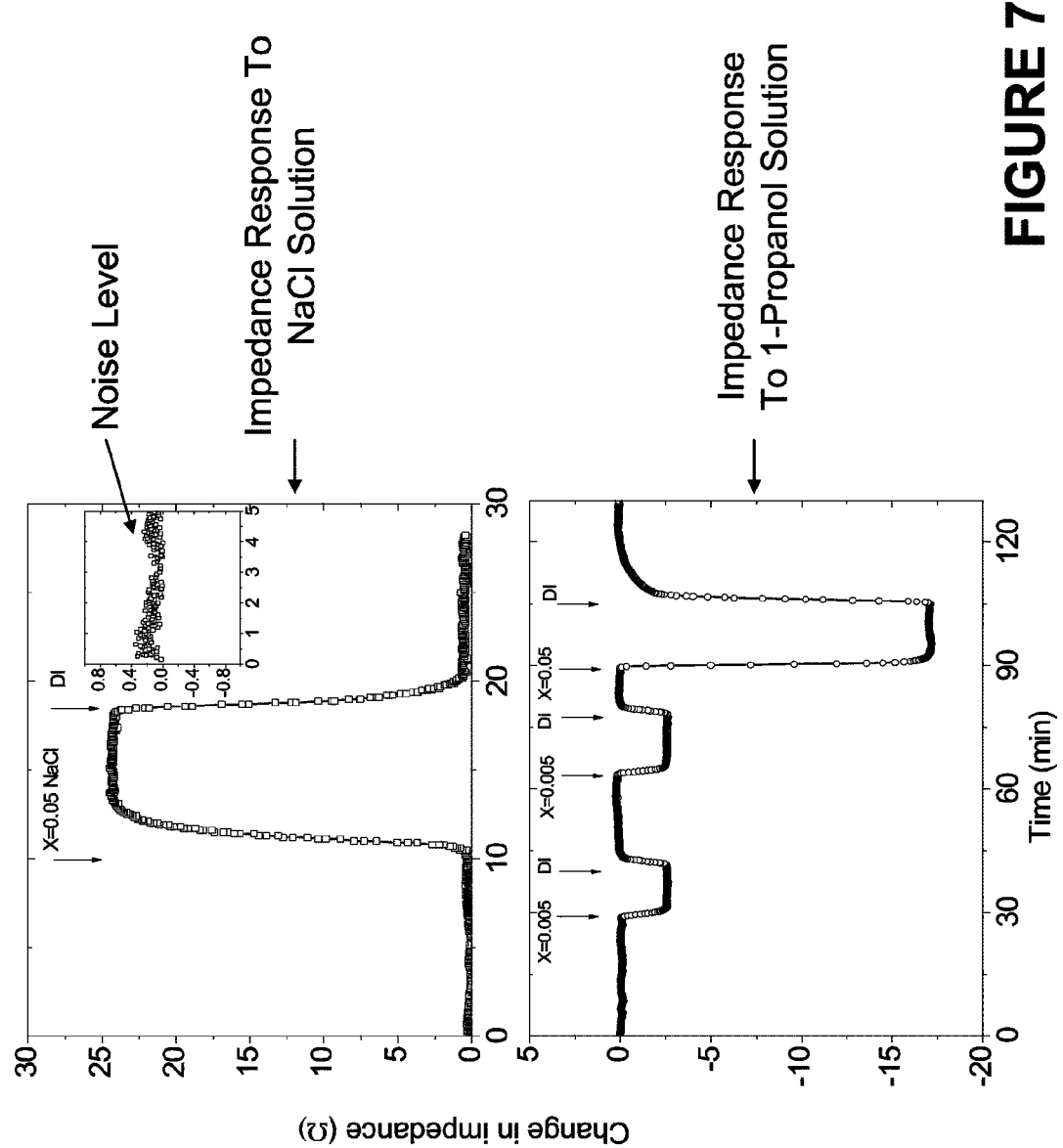
FIG. 7 illustrates an example total impedance response of a piezoelectric cantilever sensor to density change.

FIG. 7 illustrates an example total impedance response of a piezoelectric cantilever sensor to density change. Continuous flow apparatus provided a real-time measuring ability of sensor response as it was subjected to density change. The flow rate was 0.6 mL/min and the test solutions were not re-circulated to avoid cross contamination. The upper graph of FIG. 7 shows a total impedance response from DI water (X=0, ρ=0.9985 g/mL) to NaCl-solution (X=0.05, ρ=1.03403 g/mL) at monitoring frequency of f=859 kHz. After the piezoelectric cantilever sensor was stabilized in flowing DI water, NaCl-solution was introduced into the flow loop while shutting off the inflowing DI water. The total volume of flow loop was ~4 mL, and a 15 minute run ensured the entire system was filled with the NaCl-solution. Once the flow loop was filled with the introduced NaCl-solution, a new stable value was reached and showed a total impedance increase of 24.34Ω. After stabilization for 5 min, DI water was re-introduced to replace NaCl-solution, and the total impedance returned to the original value.

The lower graph of FIG. 7 shows an example density change response conducted with 1-propanol solutions at two concentrations. The experimental conditions are the same as in the upper graph of FIG. 7. After sensor was stabilized, 1-propanol solution (X=0.005, ρ=0.9978 g/mL) was introduced and the impedance change was recorded. The impedance decreased sharply by 2.59Ω and reached a steady state value in ~3 min. A repeat of DI water to same density 1-propanol solution change gave an identical response. For the third cycle, a higher mass fraction of 1-propanol (X=0.05, ρ=0.9914 g/mL) was used, and a 17.10Ω decrease was observed. Since the 1-propanol solution is lighter than DI water, the decrease in total impedance is expected. The noise level of the impedance measurement in flow system was ±0.1Ω as shown in the insert graph of the upper graph of FIG. 7. Compared with the response magnitude obtained for density changes, the signal to noise ratio is quite high (S/N=25 to 240) in these sensing experiments. The results of the above flow experiments show impedance measurement is a comparable alternate approach to monitoring resonant frequency.

Detection of *E. coli* O157:H7 Using Impedance Measurement

Figure 8:
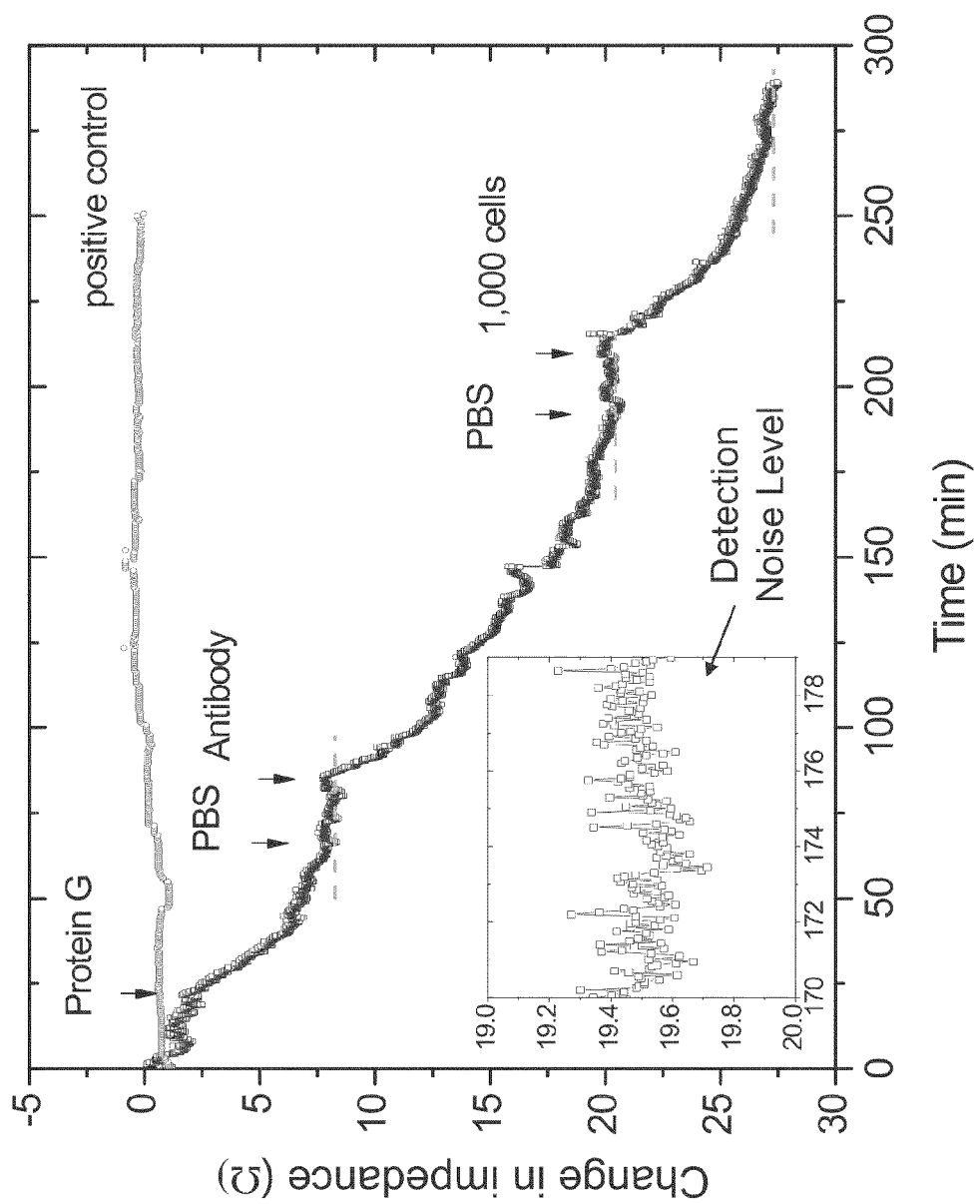
FIG. 8 illustrates detection of *E. coli* O157:H7 using total impedance.

FIG. 8 illustrates detection of *E. coli* O157:H7 using total impedance. To further test the impedance approach as a practical method in biosensing experiments, pathogen detection experiments were conducted. In this experiment, the use of the herein described impedance approach for *E. coli* O157:H7 detection was examined. As shown in FIG. 8, the experiment was conducted in a flow apparatus at 0.8 mL/min and 25.0° C. After the sensor stabilized in PBS, 1 mL of 20 μg/mL Protein G solution was introduced in re-circulation mode. A near-exponential increase of 5.66Ω was observed as Protein G bound to Au<111> sites on the sensor surface in 40 min. Followed by PBS rinse, 1 mL of 20 μg/mL antibody was injected and resulted in a further 12.51Ω near-exponential increase of impedance. At t=215 min 1,000 *E. coli* O157:H7 cells were introduced into the flow loop, and the sample was allowed to re-circulate. A 6.63Ω increase in impedance was observed due to the binding of *E. coli* O157:H7 cells to the sensor surface. The noise level was low (±0.20Ω) and signal to noise ratio was greater than 30. The increase of impedance as the cells attached is in the same direction as was the response to density increase. Control experiments with sensors that did not have gold coating showed no response (±0.5Ω) to Protein G, antibody or *E. coli* O157:H7 cells, thus confirming that the increase of impedance was indeed due to the pathogen binding. The binding rate constant k was calculated as 0.053±0.002 $min^{-1}$. The above results show that the impedance measurement of piezoelectric cantilever sensor response is a feasible method for monitoring pathogen detection.

It was experimentally shown that impedance response is feasible for detection and measurement of an analyte using an electromechanical resonating sensor. Experimentally it was found that monitoring frequency for impedance change could be located within ±1 kHz of resonant frequency. The impedance approach was verified using density change (both increase and decrease) experiments and antibody-based *E. coli* O157:H7 detection experiments. The impedance approach is applicable to scenarios in which small changes in Q-value occur, such as in biosensing applications.

Further, monitoring impedance at a fixed frequency exhibited a significantly larger response and superior signal-to-noise ratio than resonance frequency or impedance at resonance frequency monitoring approaches. The impedance approach is simple compared to the conventional resonance frequency monitoring methods and is effective for applications that require simultaneous monitoring of multiple sensors.

For sensors that have modest Q-values, the accuracy with which the resonance frequency can be measured is smaller and hence is expected to have significant noise associated with the response. As such, consideration in selecting a monitoring method for sensors with modest Q-values is the signal-to-noise ratio. In the vicinity of resonance frequency the slope of the impedance change with frequency is maximum and thus the change in impedance measured at this fixed frequency should yield a large sensing signal and at a superior signal to noise (S/N) ratio compared to either impedance at resonance frequency ($Z(f_R^r)$) or resonant frequency ($f_R^r$) itself.

Noise levels and signal-to-noise ratios of $Z(f_R^r)$ and $Z(f_R^0 \pm \alpha)$ responses were analyzed and compared with the resonance frequency ($f_R^r$) response. Noise level was calculated as the standard deviation over 5 minutes of sensor signal (15 data points) at steady state in frequency or impedance responses. The sampling rate of $f_R^r$ and $Z(f_R^0 \pm \alpha)$ responses were the same. Noise levels in $Z(f_R^0 \pm \alpha)$ response measured at each of the monitoring frequencies ($|\alpha|=0$-$25$ kHz). The measured noise levels in $Z(f_R^r)$ response was $0.037\Omega$ in comparison to noise-levels in $Z(f_R^0 \pm \alpha)$ responses that were between $0.008\Omega$ at $\alpha=0$ kHz and $0.015\Omega$ at $\alpha=+20$ kHz for the various fixed frequencies examined. The results indicate that data collected at resonance frequency will inherently have higher noise levels. The noise level in the impedance response was lowest for $\alpha=0$ kHz, and increased for fixed frequencies on either side of $f_R^0$, indicating that monitoring impedance at the initial resonant frequency ($f_R^0$) provides high quality signals. A low noise and large sensor response signal at $\alpha=0$ kHz suggests that impedance at the initial resonant frequency could be monitored for fixed frequency measurements.

The signal-to-noise ratios in $f_R^r$, $Z(f_R^r)$ and $Z(f_R^0 \pm \alpha)$ responses for the three test solutions were determined. The signal-to-noise ratios in the $Z(f_R^0 \pm \alpha)$ response at all fixed frequencies away from $f_R^0$ decreased and was maximum for $\alpha=0$ kHz. This is due to larger signals and smaller noise levels observed in the impedance responses in the vicinity of $f_R^0$. The signal-to-noise ratio of $Z(f_R^0 \pm \alpha)$ response at $\alpha=-1, 0, +1$ kHz in response to 0.2 M NaCl solutions was 97, 107 and 98, respectively. On the other hand the $Z(f_R^r)$ response exhibited a signal-to-noise ratio of 2, which is about 50-fold smaller than impedance measured at fixed frequency, $\alpha=0$ kHz. The noise level and the signal-to-noise ratio measured for the resonance frequency response was 37 Hz and 18, respectively. The traditional method of resonant frequency monitoring ($f_R^r$) exhibited greater S/N than the value for $Z(f_R^r)$ response but significantly lower than $Z(f_R^0 \pm \alpha)$ response. These results indicate that monitoring impedance changes at a fixed frequency at $\alpha=0$ kHz is superior to monitoring resonant frequency or impedance at resonant frequency.

Thus, monitoring impedance change at a fixed frequency near the initial resonant frequency of a electromechanical resonating sensor exhibited 5-fold increase in response in comparison to impedance at resonant frequency. The impedance responses were highest when the selected fixed frequency was equal to the initial resonant frequency ($\alpha=0$ kHz). The signal-to noise ratio of resonant frequency ($f_R^r$) was 5-fold smaller and impedance at resonance ($Z(f_R^r)$) was 50-fold smaller than impedance at fixed frequency. A improvement in the signal to noise ratio observed experimentally indicates that this method of monitoring sensor responses is suitable for sensors with low Q-values.

Electromechanical Resonating Sensors

A type of electromechanical resonating sensor is a piezoelectric cantilever sensor. A piezoelectric cantilever sensor (also referred to as piezoelectric cantilever sensor) as described herein provides the ability to detect and measure extremely small amounts of an analyte. The piezoelectric cantilever sensor can be utilized to detect and measure an analyte immersed in a liquid and an analyte contained in a gas or vacuum. In various example configurations, the piezoelectric cantilever sensor comprises at least one piezoelectric layer and at least one non-piezoelectric layer, wherein the piezoelectric layer is coupled to the non-piezoelectric layer such that the piezoelectric layer and the non-piezoelectric layer are not coextensive. The piezoelectric layer, the non-piezoelectric layer, or both can be coupled to at least one base. The piezoelectric layer and the non-piezoelectric layer can be of varying widths, lengths, and thicknesses.

The piezoelectric cantilever sensor is utilizable to determine the mass of an analyte accumulated thereon. In an example embodiment, a portion of the piezoelectric cantilever sensor is placed in a medium (e.g., liquid, gas, vacuum). While in the medium, a resonance frequency and/or impedance of the piezoelectric cantilever sensor is measured and compared to a baseline resonance frequency and/or impedance. The difference in the measured resonance frequency/impedance and the baseline resonance frequency/impedance is indicative of an amount of mass of analyte accumulated (e.g., bound, adsorbed, absorbed) on the piezoelectric cantilever sensor.

Analytes can be directly or indirectly bound to the surface of the non-piezoelectric portion of the piezoelectric cantilever sensor. Binding of an analyte to the non-piezoelectric portion of the piezoelectric cantilever sensor results in a change in mass of the piezoelectric cantilever sensor, a change in stiffness of the piezoelectric cantilever sensor, or a combination thereof. The changes in mass and/or stiffness are measurable as changes in resonance frequency/impedance, and can be monitored and measured by an appropriate analysis device, such as an operational amplifier, an impedance analyzer, a network analyzer, an oscillator circuit, or the like, for example. Resonance frequency and impedance changes, wherein at least a portion of the piezoelectric cantilever sensor is immersed in a liquid, are detectable and measurable. Resonance frequency and impedance changes, wherein at least a portion of the piezoelectric cantilever sensor is immersed in a gas or a vacuum, also are detectable and measurable.

The piezoelectric cantilever sensor is operable at high frequencies, such as, on the order of 0.1 MHz. to 6 MHz, for example. At these high frequencies, a Q factor (the ratio of the resonance peak frequency relative to the resonance peak width at half peak height), on the order of 10 to 100, under liquid immersion is obtainable. The piezoelectric cantilever sensor is operable at relative high frequencies in liquid media, gas media, and a vacuum. The piezoelectric cantilever sensor thus provides extreme sensitivity to mass changes. The piezoelectric cantilever sensor is especially suitable for analytes that are present at very low concentrations in media such as in body fluids, water, and food materials, for example.

The piezoelectric cantilever sensor described herein provides the ability to detect changes in mass accumulated thereon as small as 100 attogram/Hz ($100 \times 10^{-18}$ grams/Hertz) or less when immersed in a liquid media. Thus, with respect to detecting changes in mass, the piezoelectric cantilever sensor is approximately 1 million times more sensitive than a quartz crystal micro-cantilever sensor, approximate 100,000 times more sensitive than standard analytical instruments, and about 10,000 times more sensitive than conventional, three-layer piezoelectric cantilever designs.

The piezoelectric cantilever sensor permits detection of extremely small concentrations of analyte that bind to the non-piezoelectric portion thereof. Utilizing the piezoelectric cantilever sensor, pathogens and proteins are detectable at concentrations as low as a few pathogens/mL and, for proteins of average size (60 kilo-Daltons, kDa), at less than 1 pathogen/mL. Furthermore, any analyte that binds to an organic or inorganic functional group on the non-piezoelectric portion is detectable. The piezoelectric cantilever sensor is operable in media having relatively high flow rates. The piezoelectric cantilevers sensors is operable in media having flow rates of 0.5 to 10.0 mL/minute, which is approximately 1000 times the flow rate used successfully with known bending mode micro-cantilevers.

Various example applications of the piezoelectric cantilever include the detection of bioterrorism agents, such as *Bacillus anthracis*, the detection of food-borne pathogens, such as *E. coli*, the detection of pathogens in food and water, the detection of certain cell types in body fluids (e.g., circulating tumor cells), the detection of biomarkers in body fluids (e.g., proteins that mark specific pathophysiology-alpha-fetoprotein, beta-2-microglobulin, bladder tumor antigen, breast cancer marker CA-15-3, and other CAs (cancer antigens), calcitonin, carcinoembryonic antigen, and others), the detection of markers of explosives such as trinitrotoluene, the presence of dinitrotoluene, and the detection of airborne and waterborne toxins. The piezoelectric cantilever sensor also can be used for the detection of biological entities at picogram levels, and for the detection of protein-protein interactions, both steady state and kinetic.

Pathogens, such as *E coli* for example, are detectable utilizing the piezoelectric cantilever sensor. Detection of a model protein, lipoprotein, DNA, and/or RNA at a concentration 1.0 femtogram per mL ($10^{-15}$ grams) and pathogens at 1 pathogen/mL, respectively is achievable by measuring directly in liquid using the piezoelectric cantilever sensor immobilized with antibodies specific to the target analyte at a frequency of about 1 to 2 MHz. The piezoelectric cantilever sensor is capable of detecting a target analyte without false positives or negatives even when contaminating entities are present. The piezoelectric cantilever sensor described herein is particularly advantageous when utilized with a raw sample, and no preparation, concentrating step, and/or enrichment of any type. Detection of an analyte utilizing the piezoelectric cantilever sensor can be conducted directly in raw samples under flow conditions, such as 0.5 to 10.0 mL/minute for example. If clean samples are available, such as in a laboratory environment, detection at 1 femtogram/mL is achievable. This sensitivity is approximately 100 times more sensitive than the sensitivity associated with known optical techniques.

As described below, the sensitivity of the piezoelectric cantilever sensor is due in part to the geometric design thereof. The relative lengths and widths of the piezoelectric and non-piezoelectric layers of the piezoelectric cantilever sensor determine the sensitivity, and also the shape of the peak of the frequency and/or impedance spectrum provided by the piezoelectric cantilever sensor. As described in more detail below, the piezoelectric cantilever sensor comprises a piezoelectric layer and a non-piezoelectric layer coupled together such that a portion of the piezoelectric layer extends beyond the non-piezoelectric layer, or a portion of the non-piezoelectric layer extends beyond the piezoelectric layer, or a combination thereof. Thus, the piezoelectric layer and the non-piezoelectric layer are not coextensive. That is, the piezoelectric cantilever sensor is configured such that an entire surface of the non-piezoelectric layer is not coupled to an entire surface of the piezoelectric layer.

The sensitivity of the piezoelectric cantilever sensor is due in part to utilizing the piezoelectric layer of the cantilever sensor for both actuation and sensing and the electromechanical properties of the piezoelectric layer of the piezoelectric cantilever sensor. At resonance, the oscillating cantilever concentrates stress in the piezoelectric layer toward a base portion of the self-exciting, self-sensing piezoelectric cantilever. This results in an amplified change in the resistive component of the piezoelectric layer, and a large shift in resonance frequency. Directing this stress to a portion of the piezoelectric layer having a low bending modulus (e.g., more flexible) allows for exploitation of the associated shift in resonance frequency to detect extremely small changes in mass of the piezoelectric cantilever sensor. For example, if both the piezoelectric layer and the non-piezoelectric layer of a piezoelectric cantilever sensor are anchored at the same end (e.g., potted in epoxy), the sensor is less sensitive to changes in mass because the bending stress in the sensing piezoelectric layer proximal to the anchored end is lower compared to the case when only the piezoelectric layer is anchored. This is because the bending modulus of the two combined layers is higher than the case of anchoring the piezoelectric layer only. Bending modulus is the product of elastic modulus and moment of inertia about the neutral axis. And, moment of inertia is proportional to the cube power of thickness.

Figure 9:
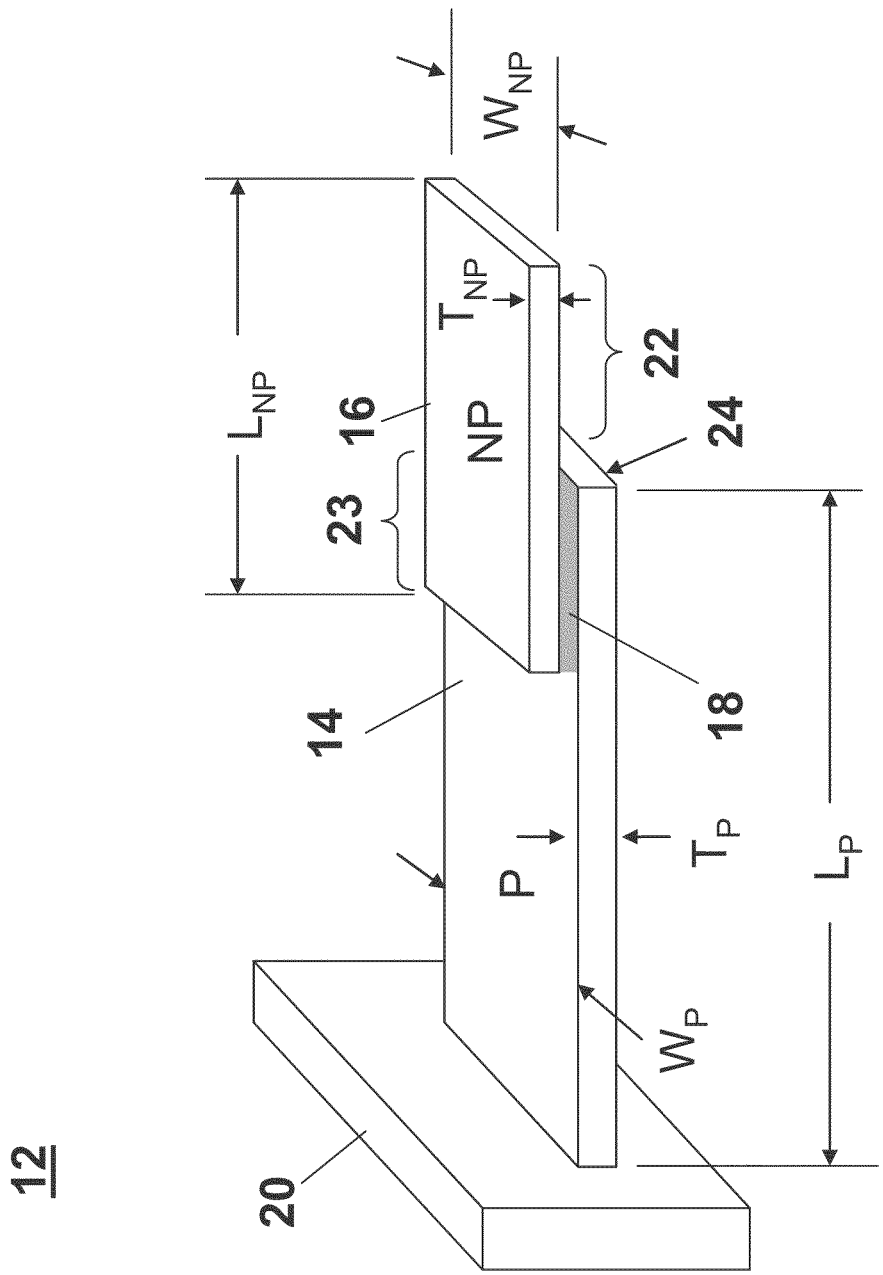
FIG. 9 is an illustration of a piezoelectric cantilever sensor comprising a piezoelectric portion and a non-piezoelectric portion.

FIG. 9 is an illustration of a piezoelectric cantilever sensor 12 comprising a piezoelectric portion 14 and a non-piezoelectric portion 16. Piezoelectric portions are labeled with an uppercase letter p ("P"), and non-piezoelectric portions are labeled with the uppercase letters np ("NP"). The piezoelectric cantilever sensor 12 depicts an embodiment of an unanchored, overhang, piezoelectric cantilever sensor. The piezoelectric cantilever sensor 12 is termed "unanchored" because the non-piezoelectric layer 16 is not attached to the base portion 20. The piezoelectric cantilever sensor 12 is termed, "overhang" because the non-piezoelectric layer 16 extends beyond the distal tip 24 of the piezoelectric layer 14 to create an overhanging portion 22 of the non-piezoelectric layer 16. The piezoelectric portion 14 is coupled to the non-piezoelectric portion 16 via adhesive portion 18. The piezoelectric portion 14 and the non-piezoelectric portion overlap at region 23. The adhesive portion 18 is positioned between the overlapping portions of the piezoelectric portion 14 and the non-piezoelectric portion 16. The piezoelectric portion 14 is coupled to a base portion 20.

The piezoelectric portion 14 can comprise any appropriate material such as lead zirconate titanate, lead magnesium niobate-lead titanate solid solutions, strontium lead titanate, quartz silica, piezoelectric ceramic lead zirconate and titanate (PZT), piezoceramic-polymer fiber composites, or the like, for example. The non-piezoelectric portion 16 can comprise any appropriate material such as glass, ceramics, metals, polymers and composites of one or more of ceramics, and polymers, such as silicon dioxide, copper, stainless steel, titanium, or the like, for example.

The piezoelectric cantilever sensor can comprise portions having any appropriate combination of dimensions. Further, physical dimensions can be non-uniform. Thus, the piezoelectric layer and/or the non-piezoelectric layer can be tapered. For example, the length (e.g., $L_P$ in FIG. 9) of the piezoelectric portion (e.g., piezoelectric portion 14) can range from about 0.1 to about 10 mm. The length (e.g., $L_{NP}$ in FIG. 9) of the non-piezoelectric portion (e.g., non-piezoelectric portion 16) can range from about 0.1 to about 10 mm. The overlap region (e.g., overlap region 23) can range from about 0.1 to about 10 mm in length. The width (e.g., $W_P$ in FIG. 9) of the piezoelectric portion (e.g., piezoelectric portion 14), and the width (e.g., $W_{NP}$ in FIG. 9) of the non-piezoelectric portion (e.g., non-piezoelectric portion 16), can range from about 0.1 mm to about 4.0 mm. The width (e.g., $W_P$ in FIG. 9) of the piezoelectric portion can differ from the width (e.g., $W_{NP}$ in FIG. 9) of the non-piezoelectric portion as well. The thickness of the (e.g., $T_P$ in FIG. 9) of the piezoelectric portion (e.g., piezoelectric portion 14), and the thickness (e.g., $T_{NP}$ in FIG. 9) of the non-piezoelectric portion (e.g., non-piezoelectric portion 16), can range from about 10 micrometers ($10 \times 10^{-6}$ meters) to about 4.0 mm. The thickness (e.g., $T_P$ in FIG. 9) of the piezoelectric portion also can differ from the thickness (e.g., $T_{NP}$ in FIG. 9) of the non-piezoelectric portion.

Figure 10:
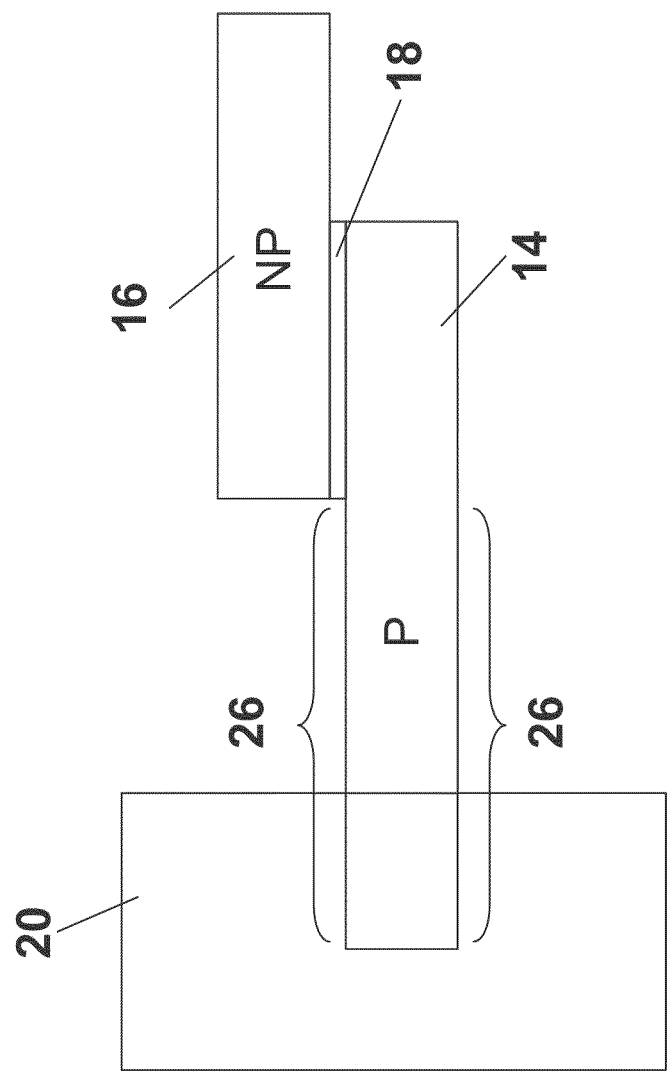
FIG. 10 is a cross-sectional view of the piezoelectric cantilever sensor depicting electrode placement regions for electrodes operatively associated with the piezoelectric portion.
Figure 11:
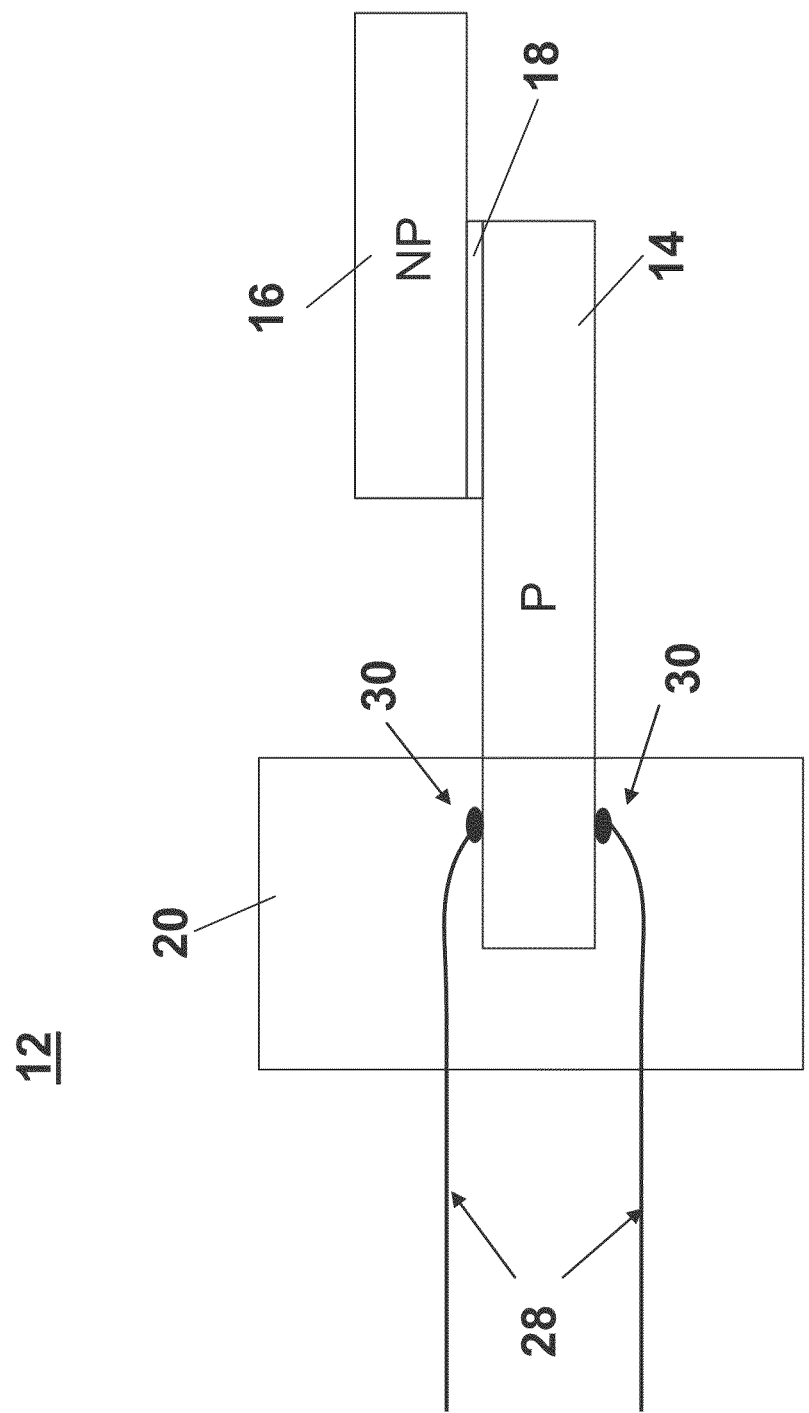
FIG. 11 illustrates an example electrode placement on the piezoelectric cantilever sensor.
Figure 12:
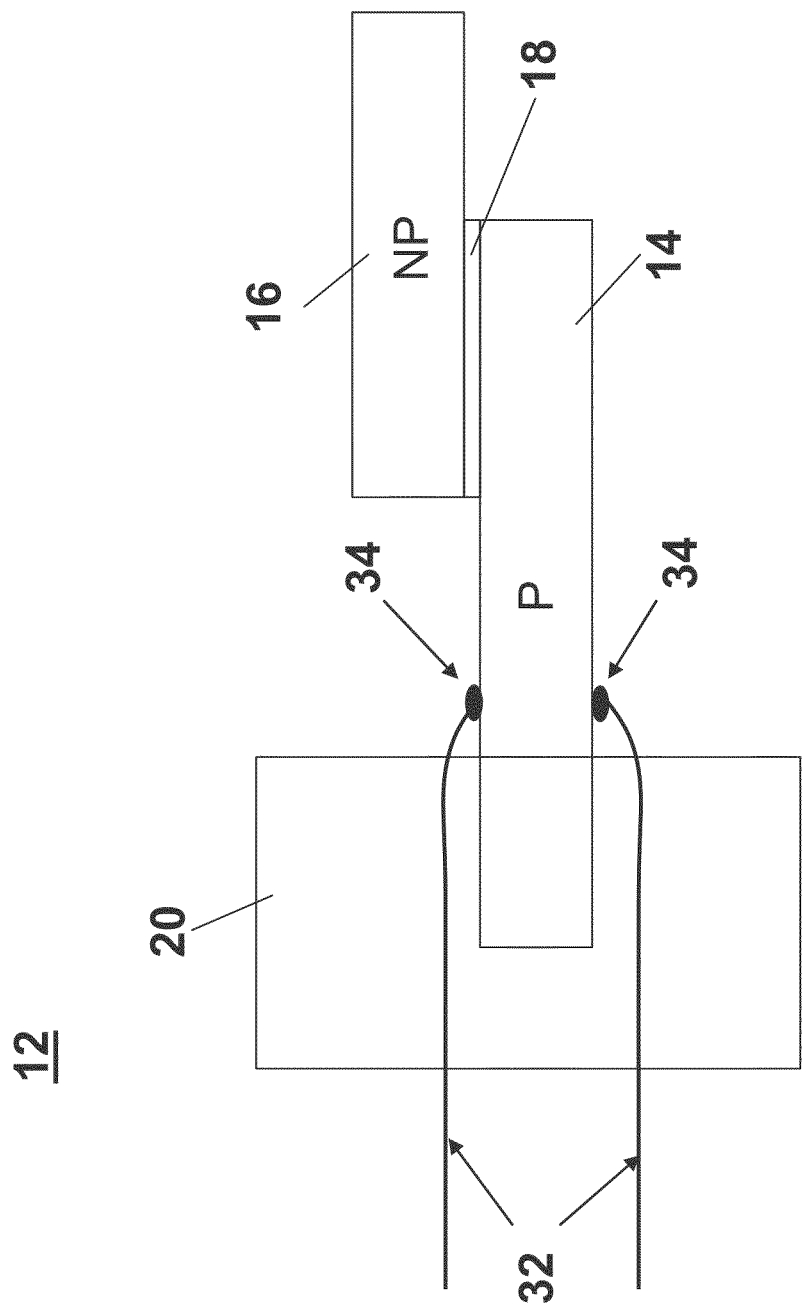
FIG. 12 illustrates another example electrode placement on the piezoelectric cantilever sensor.

FIG. 10 is a cross-sectional view of the piezoelectric cantilever sensor 12 depicting electrode placement regions 26 for electrodes operationally associated with the piezoelectric portion 14. Electrodes can be placed at any appropriate location on the piezoelectric portion of the piezoelectric cantilever sensor as indicated by brackets 26. For example, as shown in FIG. 11, electrodes 28 can be coupled to the piezoelectric portion 14 within the base portion 20. Or, as depicted in FIG. 12, electrodes 32 can be coupled to the piezoelectric portion 14 at any location not within the base portion 20 and not overlapped by the non-piezoelectric portion 16. Electrodes need not be placed symmetrically about the piezoelectric portion 14. In an example embodiment, one electrode can be coupled to the piezoelectric portion 14 within the base portion 20 and the other electrode can be coupled to the piezoelectric portion 14 not within the base portion 20. Electrodes, or any appropriate means (e.g., inductive means, wireless means), can be utilized to provide an electrical signal to and receive an electrical signal from the piezoelectric portion 14. In an example embodiment, electrodes can be coupled to the piezoelectric portion 14 via a bonding pad or the like (depicted as elements 30 in FIG. 11 and elements 34 in FIG. 12). Example bonding pads can comprise any appropriate material (e.g., gold, silicon oxide) capable of immobilization of a receptor material and/or an absorbent material appropriate for use in chemical sensing or for bio-sensing.

Electrodes can be placed at any appropriate location. In an example embodiment, electrodes are operatively located near a location of concentrated stress in the piezoelectric layer 14. As described above, the sensitivity of the piezoelectric cantilever sensor is due in part to advantageously directing (concentrating) the stress in the piezoelectric layer 14 and placing electrodes proximate thereto. The configurations of the piezoelectric cantilever sensor described herein (and variants thereof) tend to concentrate oscillation associated stress in the piezoelectric layer 14. At resonance, in some of the configurations of the piezoelectric cantilever sensor, the oscillating cantilever concentrates stress in the piezoelectric layer 14 toward the base portion 20. This results in an amplified change in the resistive component of the piezoelectric layer 14, and a large shift in resonance frequency at the locations of high stress. Directing this stress to a portion of the piezoelectric layer 14 having a low bending modulus (e.g., more flexible) allows for exploitation of the associated shift in resonance frequency to detect extremely small changes in mass of the piezoelectric cantilever sensor. Thus, in example configurations of the piezoelectric cantilever sensor, the thickness of the piezoelectric layer 14 located near the base portion 20 is thinner than portions of the piezoelectric layer 14 further away from the base portion 20. This tends to concentrate stress toward the thinner portion of the piezoelectric layer 14. In example configurations, electrodes are located at or near the locations of the oscillation associated concentrated stress near the base portion of the piezoelectric cantilever sensor. In other example configurations of the piezoelectric cantilever sensor electrodes are positioned proximate the location of concentrated stress in the piezoelectric layer regardless of the proximity of the concentrated stress to a base portion of the piezoelectric cantilever sensor.

Figure 13:
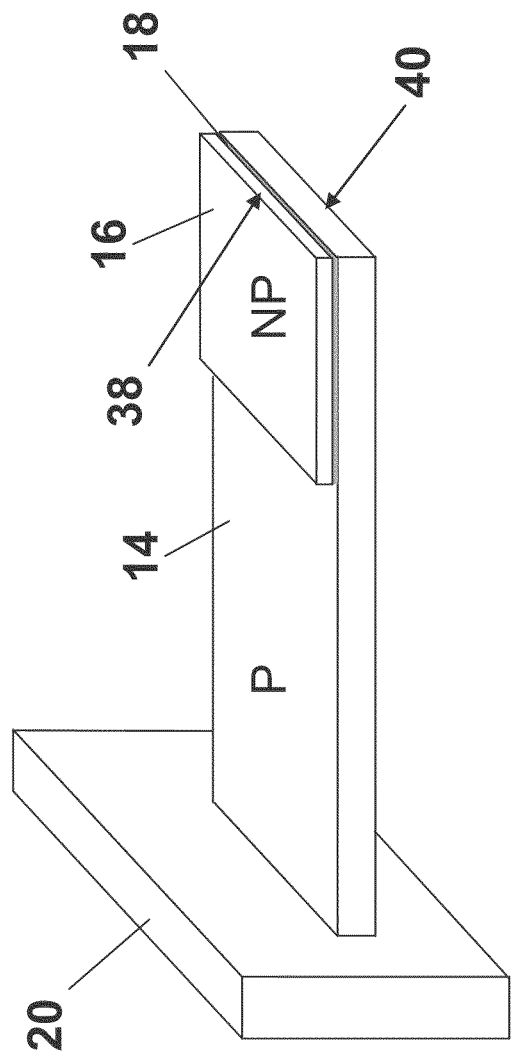
FIG. 13 is an illustration of an example configuration of an unanchored piezoelectric cantilever sensor.

The piezoelectric cantilever sensor can be configured in accordance with a plurality of configurations, some of which are depicted in FIG. 13 through FIG. 36. It is to be understood however, that the configurations depicted herein do not represent all possible configurations, but rather a representative sample of configurations of the piezoelectric cantilever sensor. FIG. 13 is an illustration of an example configuration 36 of an unanchored piezoelectric cantilever sensor wherein the distal end 40 of the piezoelectric portion 14 is flush with the distal end 38 of the non-piezoelectric portion 16. The piezoelectric cantilever sensor 36 is termed "unanchored" because the non-piezoelectric portion 16 is not attached to the base portion 20. The piezoelectric portion 14 is coupled to the non-piezoelectric portion 16 via adhesive portion 18. The adhesive portion 18 is positioned between the overlapping portions of the piezoelectric portion 14 and the non-piezoelectric portion 16. The piezoelectric portion 14 is coupled to a base portion 20.

Figure 14:
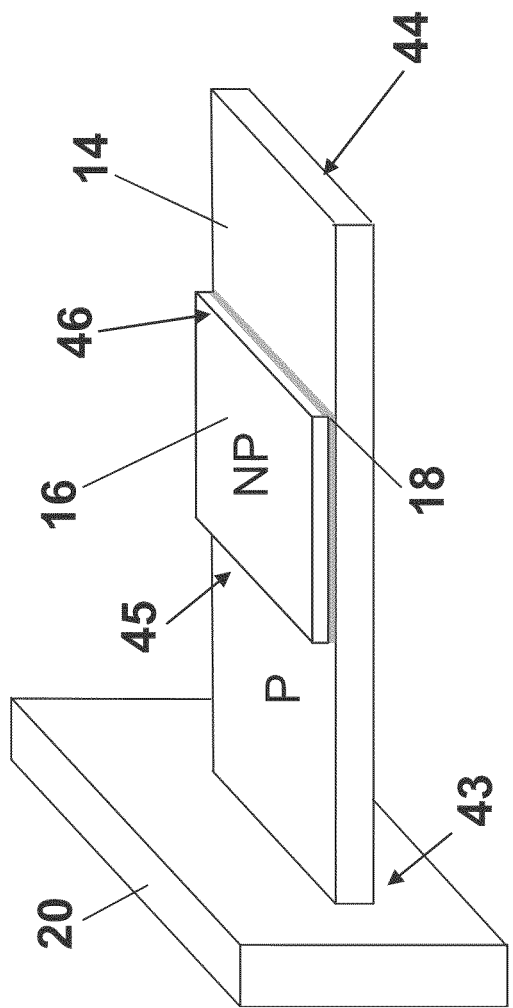
FIG. 14 is another illustration of an example configuration of an unanchored piezoelectric cantilever sensor.

FIG. 14 is an illustration of an example configuration 42 of an unanchored piezoelectric cantilever sensor wherein the distal end 44 of the piezoelectric portion 14 extends beyond the distal end 46 of the non-piezoelectric portion 16 and the proximate end 43 of the piezoelectric portion 14 extends beyond the proximate end 45 of the non-piezoelectric portion 16. The piezoelectric portion 14 is coupled to the non-piezoelectric portion 16 via adhesive portion 18. The adhesive portion 18 is positioned between the overlapping portions of the piezoelectric portion 14 and the non-piezoelectric portion 16. The piezoelectric portion 14 is coupled to the base portion 20.

The piezoelectric cantilever sensor also can be configured to comprise multiple base portions. Example configurations of the piezoelectric cantilever sensor comprising multiple base portions are depicted in FIG. 15 through FIG. 22. Configuring the piezoelectric cantilever sensor to comprise multiple base portions is not intuitive because the expectation of one skilled in the art would be that affixation of both ends of the piezoelectric cantilever sensor would provide a poor response as a result of the restrictions of the displacement of the piezoelectric cantilever sensor as a result of its affixation to the multiple base portions. For configurations of the piezoelectric cantilever sensor comprising two base portions, in an example embodiment, the stress of in the piezoelectric portion is measured, rather than the displacement of the piezoelectric portion. Configuring the piezoelectric cantilever sensor to comprise two base portions provides a stable and robust sensor that can perform under relatively high media flow conditions and provide excellent mass change sensitivity. Along with providing a mechanically robust piezoelectric cantilever sensor that can withstand a relatively wide range of media flow conditions with minimal determination in performance, configuring the piezoelectric cantilever sensor to comprise two base portions provides a fundamental frequency (e.g., greater than 100 kHz) that is three to four times higher than a cantilever sensor having a single base portion and of similar dimensions.

Figure 15:
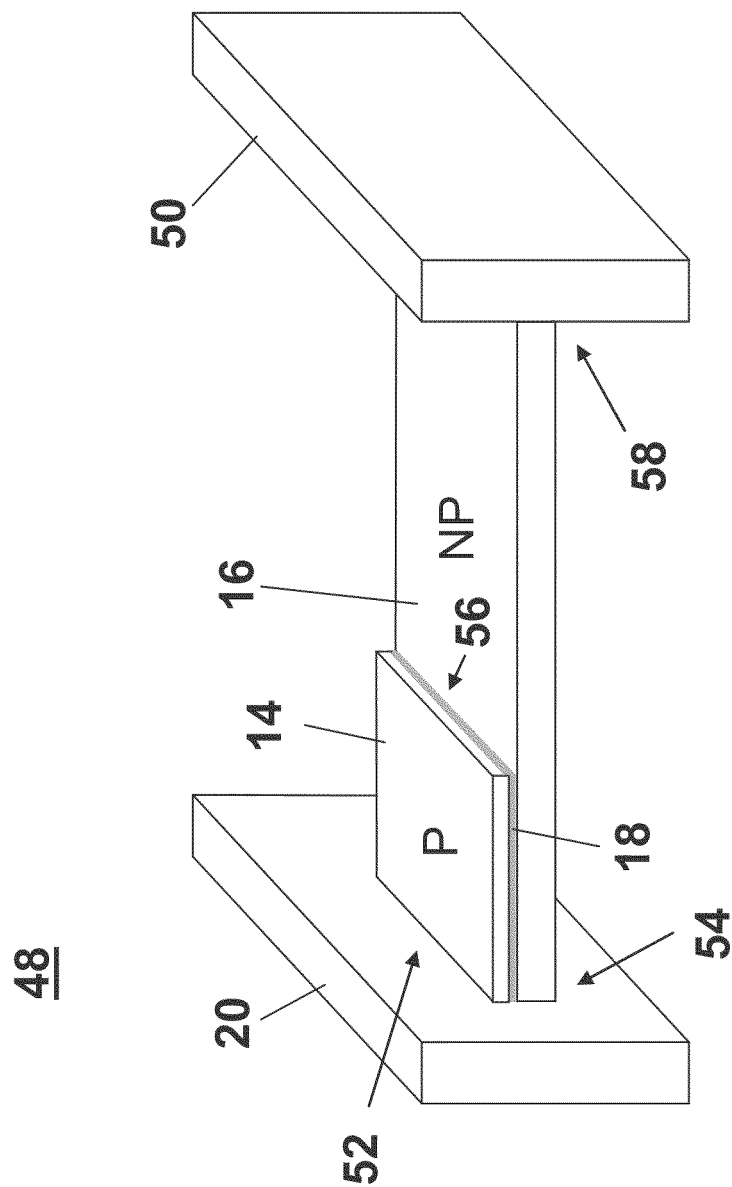
FIG. 15 is an illustration of an example configuration of an anchored piezoelectric cantilever sensor comprising two base portions.

FIG. 15 is an illustration of an example configuration 48 of an anchored piezoelectric cantilever sensor comprising two base portions 20, 50. The piezoelectric cantilever sensor 48 is termed "anchored" because the non-piezoelectric portion 16 is attached to the base portion 20. In the configuration depicted in the piezoelectric cantilever sensor 48, both the proximate end 52 of the piezoelectric portion 14 and the proximate end 54 of the non-piezoelectric portion 16 are attached to the base portion 20. The piezoelectric portion and the non-piezoelectric portion can be attached to the base portion via any appropriate means. The distal end 58 of the non-piezoelectric portion 16 also is attached to the base portion 50. The distal end 58 of the non-piezoelectric portion 16 extends beyond the distal portion 56 of the piezoelectric portion 14. The piezoelectric portion 14 is coupled to the non-piezoelectric portion 16 via adhesive portion 18. The adhesive portion 18 is positioned between the overlapping portions of the piezoelectric portion 14 and the non-piezoelectric portion 16.

Figure 16:
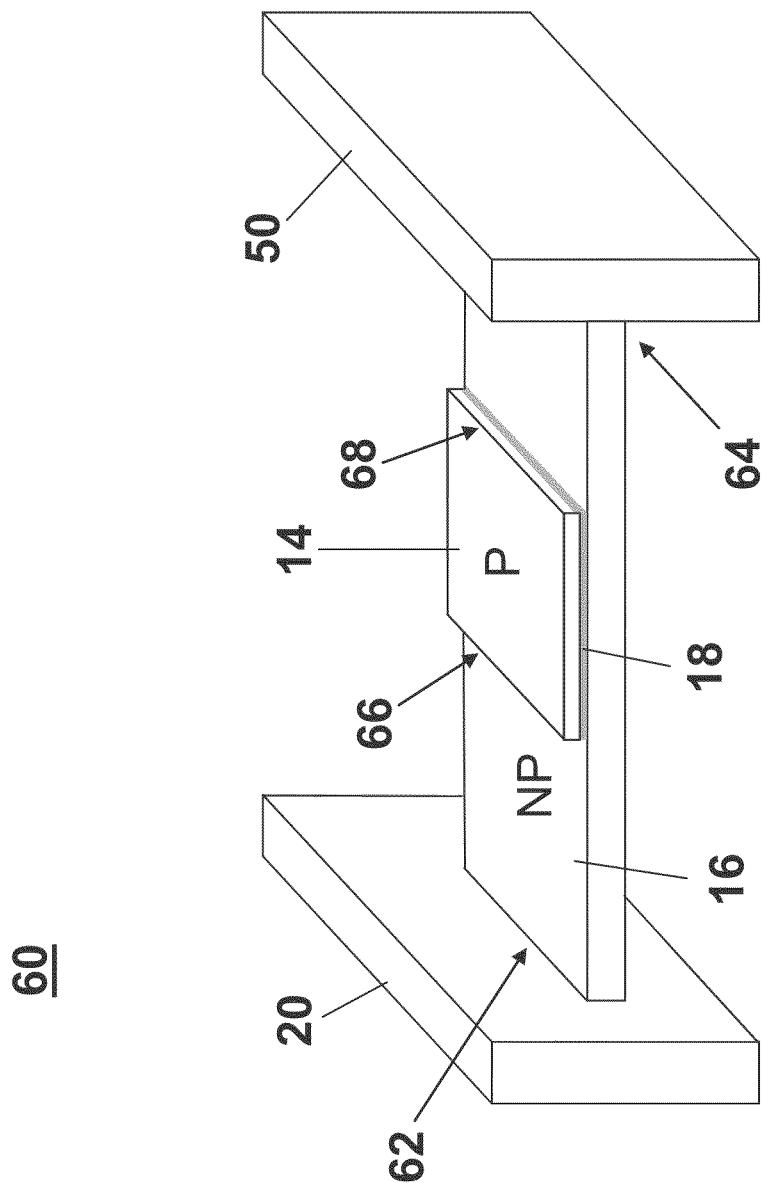
FIG. 16 is another illustration of an example configuration of an anchored piezoelectric cantilever sensor comprising two base portions.

FIG. 16 is an illustration of an example configuration 60 of an anchored piezoelectric cantilever sensor comprising two base portions 20, 50, wherein the piezoelectric portion 14 is not attached to either base portion 20 or base portion 50. In the configuration depicted in the piezoelectric cantilever sensor 60, the proximate end 62 of the non-piezoelectric portion 16 is attached to the base portion 20 and the distal end 64 of the non-piezoelectric portion 16 is attached to the base portion 50. The proximate end 62 of the non-piezoelectric portion 16 extends beyond the proximate end 66 of the piezoelectric portion 14 and the distal end 64 of the non-piezoelectric portion 16 extends beyond the distal end 68 of the piezoelectric portion 14. The piezoelectric portion 14 is coupled to the non-piezoelectric portion 16 via adhesive portion 18. The adhesive portion 18 is positioned between the overlapping portions of the piezoelectric portion 14 and the non-piezoelectric portion 16.

Figure 17:
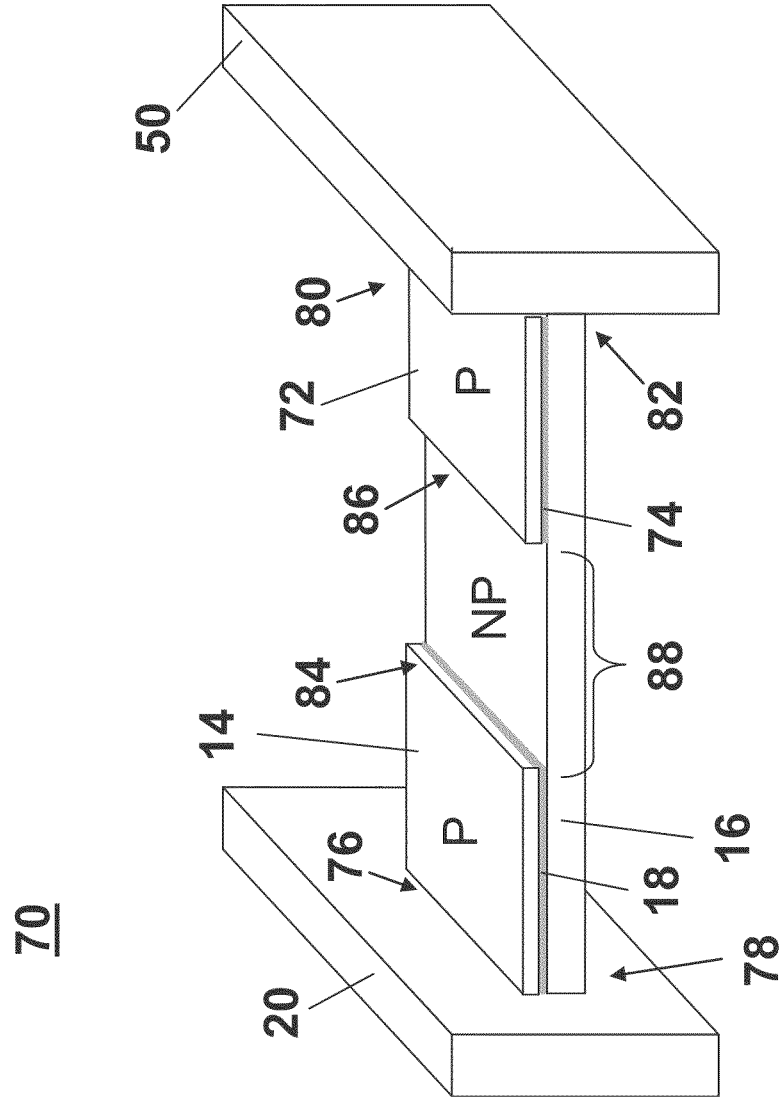
FIG. 17 is another illustration of an example configuration of an anchored piezoelectric cantilever sensor comprising two base portions.

FIG. 17 is an illustration of an example configuration 70 of an anchored piezoelectric cantilever sensor comprising two base portions 20, 50, comprising two piezoelectric portions 14, 72, and comprising two adhesive portions 18, 74. In the configuration depicted in the piezoelectric cantilever sensor 70, the proximate end 76 of the piezoelectric portion 14 and the proximate end 78 of the non-piezoelectric portion 16 are attached to the base portion 20. The distal end 80 of the piezoelectric portion 72 and the distal end 82 of the non-piezoelectric portion 16 are attached to the base portion 50. The proximate end 78 of the non-piezoelectric portion 16 extends beyond the proximate end 86 of the piezoelectric portion 72. The distal end 82 of the non-piezoelectric portion 16 extends beyond the distal end 84 of the piezoelectric portion 14. The distal end 84 of the piezoelectric portion 14 and the proximate end 86 of the piezoelectric portion 72 form a space 88 therebetween. The piezoelectric portion 14 is coupled to the non-piezoelectric portion 16 via adhesive portion 18. The piezoelectric portion 72 is coupled to the non-piezoelectric portion 16 via adhesive portion 74. The adhesive portions 18 and 74 are positioned, respectively, between the overlapping portions of the piezoelectric portion 14 and the non-piezoelectric portion 16, and the piezoelectric portion 72 and the non-piezoelectric portion 16.

Figure 18:
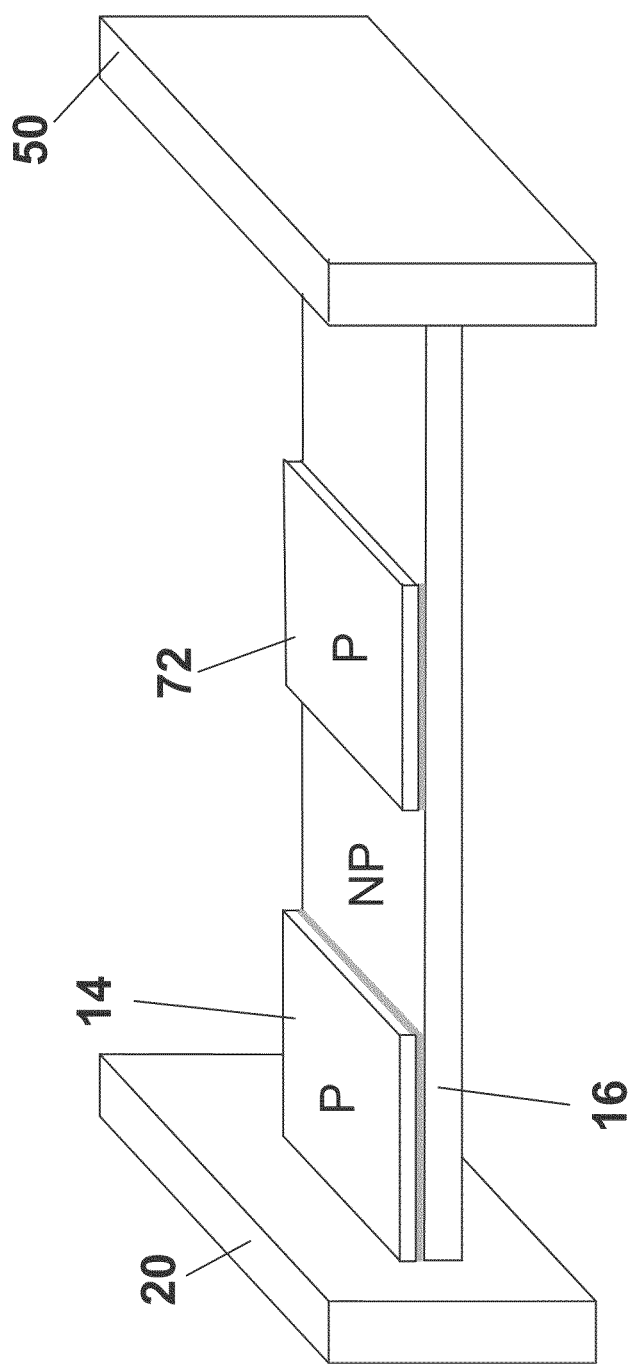
FIG. 18 is an illustration of an example configuration of a self-exciting, self-sensing piezoelectric cantilever sensor wherein the piezoelectric layer comprises two portions, one of which is anchored.
Figure 19:
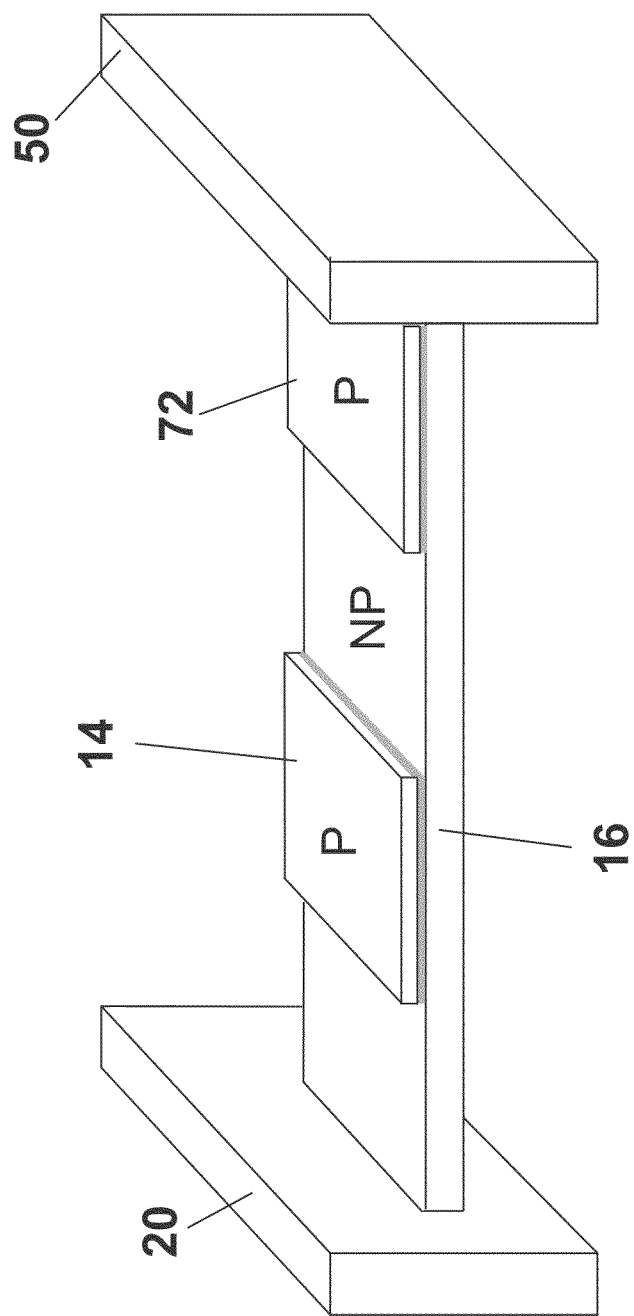
FIG. 19 is another illustration of an example configuration of a self-exciting, self-sensing piezoelectric cantilever sensor wherein the piezoelectric layer comprises two portions, one of which is anchored.
Figure 20:
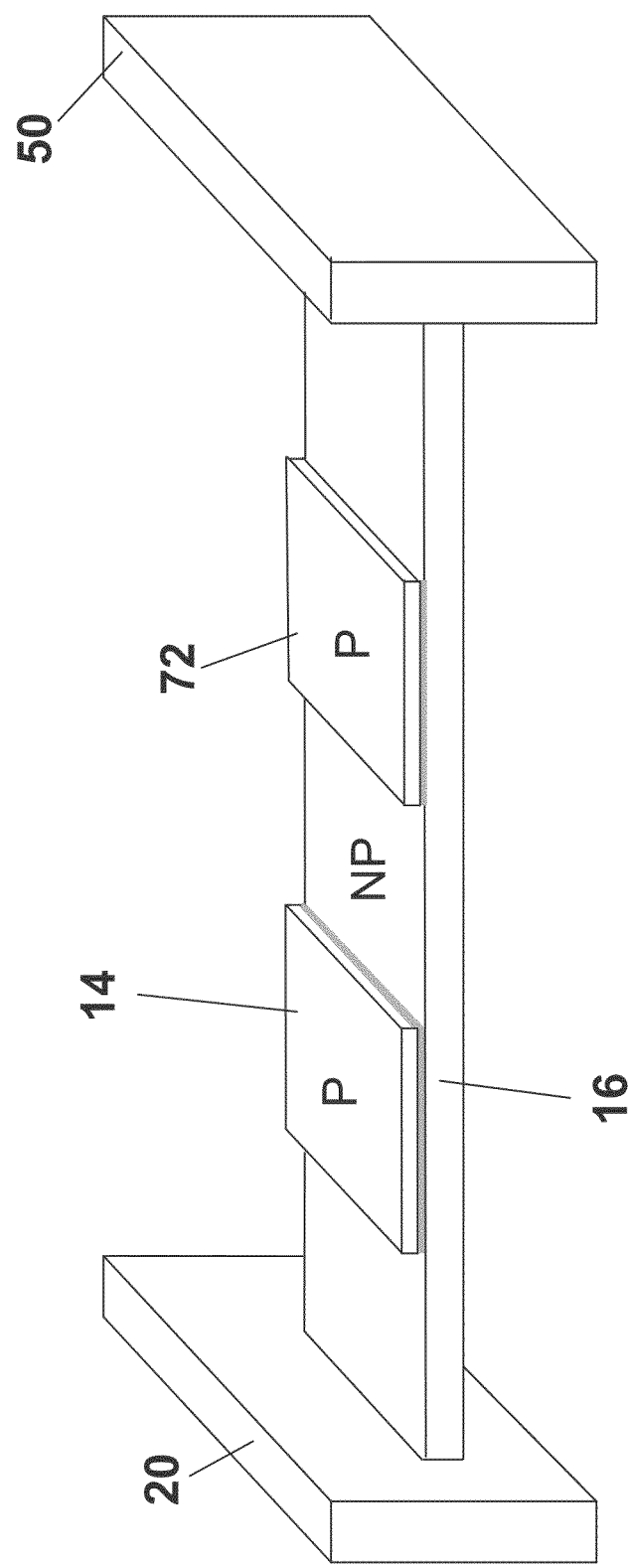
FIG. 20 is another illustration of an example configuration of a self-exciting, self-sensing piezoelectric cantilever sensor wherein the piezoelectric layer comprises two portions, one of which is anchored.

In various alternate example configurations of the configuration 70 depicted in FIG. 17, only one of the piezoelectric portions 14, 72 is attached to a respective base portion 20, 50. For example, in one example configuration as depicted in FIG. 18, the piezoelectric portion 14 is attached to the base portion 20 and the piezoelectric portion 72 is not attached to the base portion 50. In another example configuration, as depicted in FIG. 19, the piezoelectric portion 72 is attached to the base portion 50 and the piezoelectric portion 14 is not attached to the base portion 20. In yet another example configuration, as depicted in FIG. 20, neither the piezoelectric portion 14 nor the piezoelectric portion 72 is attached to a respective base portion 20, 50. In the various example configurations in which a piezoelectric layer comprises multiple portions, electrodes can be attached to any appropriate piezoelectric portion or portions. For example, in the example configuration depicted in FIG. 17, FIG. 18, FIG. 19, and FIG. 20, electrodes can be attached to piezoelectric portion 14, piezoelectric portion 72, or a combination thereof.

Figure 21:
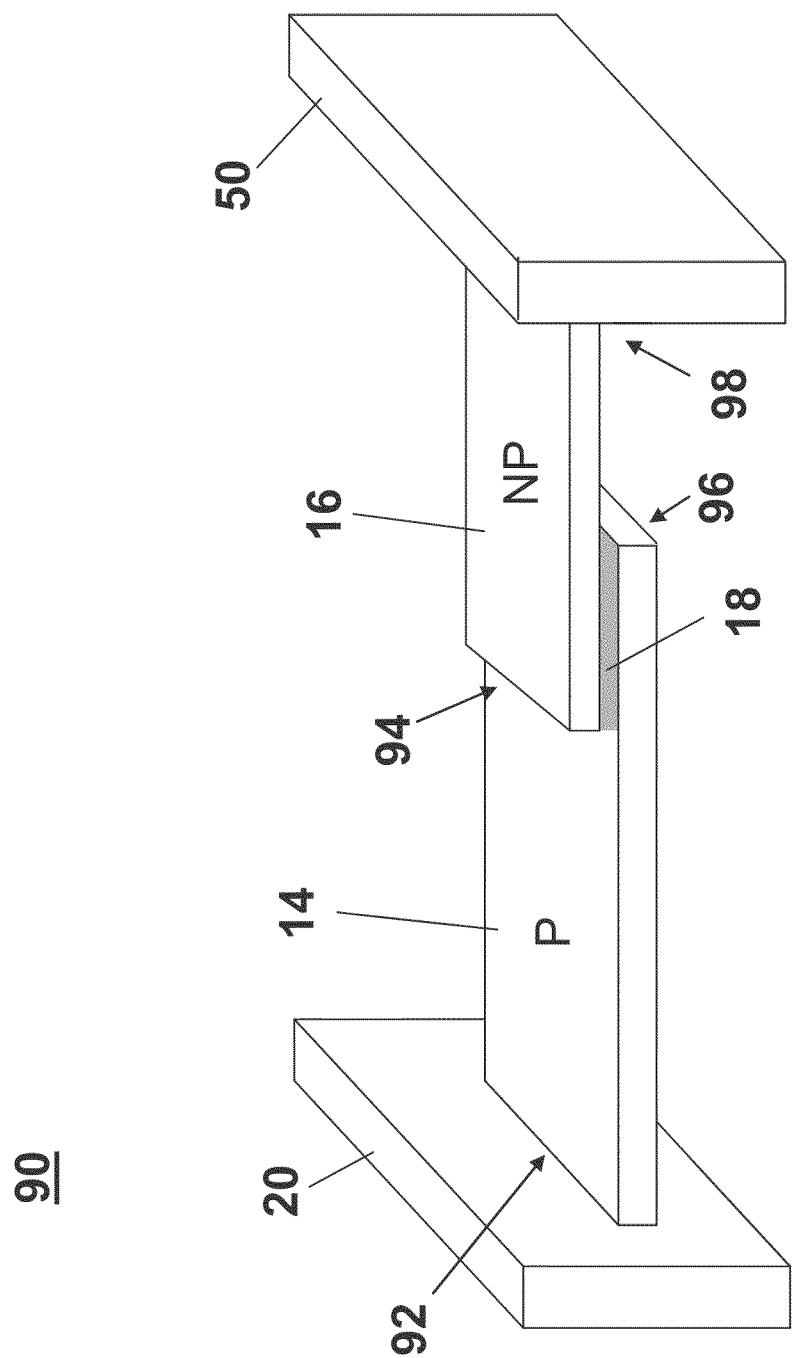
FIG. 21 is another illustration of an example configuration of an anchored piezoelectric cantilever sensor comprising two base portions.

FIG. 21 is an illustration of an example configuration 90 of an anchored piezoelectric cantilever sensor comprising two base portions 20, 50, wherein the piezoelectric portion 14 is attached to the base portion 20 and the non-piezoelectric portion 16 is attached to the base portion 50. The piezoelectric portion 14 is coupled to the non-piezoelectric portion 16 via adhesive portion 18. The adhesive portion 18 is positioned between the overlapping portions of the piezoelectric portion 14 and the non-piezoelectric portion 16. The distal end 98 of the non-piezoelectric portion 16 extends beyond the distal end 96 of the piezoelectric portion 14. The proximate end 92 of the piezoelectric portion 14 extends beyond the proximate end 94 of the non-piezoelectric portion 16.

Figure 22:
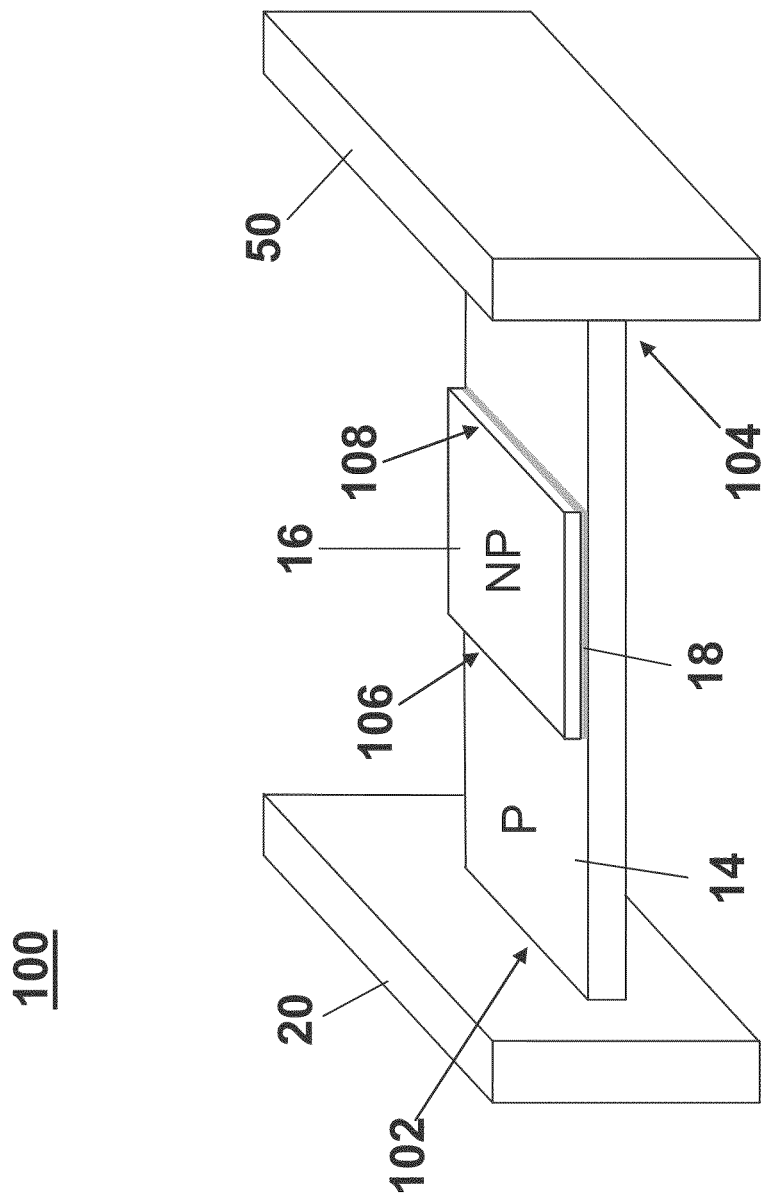
FIG. 22 is another illustration of an example configuration of an anchored piezoelectric cantilever sensor comprising two base portions.

FIG. 22 is an illustration of an example configuration 100 of an anchored piezoelectric cantilever sensor comprising two base portions 20, 50, wherein the non-piezoelectric portion 16 is not attached to either base portion 20 or base portion 50. In the configuration depicted in the piezoelectric cantilever sensor 100, the proximate end 102 of the piezoelectric portion 14 is attached to the base portion 20 and the distal end 104 of the piezoelectric portion 14 is attached to the base portion 50. The proximate end 102 of the piezoelectric portion 14 extends beyond the proximate end 106 of the non-piezoelectric portion 16 and the distal end 104 of the piezoelectric portion 14 extends beyond the distal end 108 of the non-piezoelectric portion 16. The piezoelectric portion 14 is coupled to the non-piezoelectric portion 16 via adhesive portion 18. The adhesive portion 18 is positioned between the overlapping portions of the piezoelectric portion 14 and the non-piezoelectric portion 16.

Figure 23:
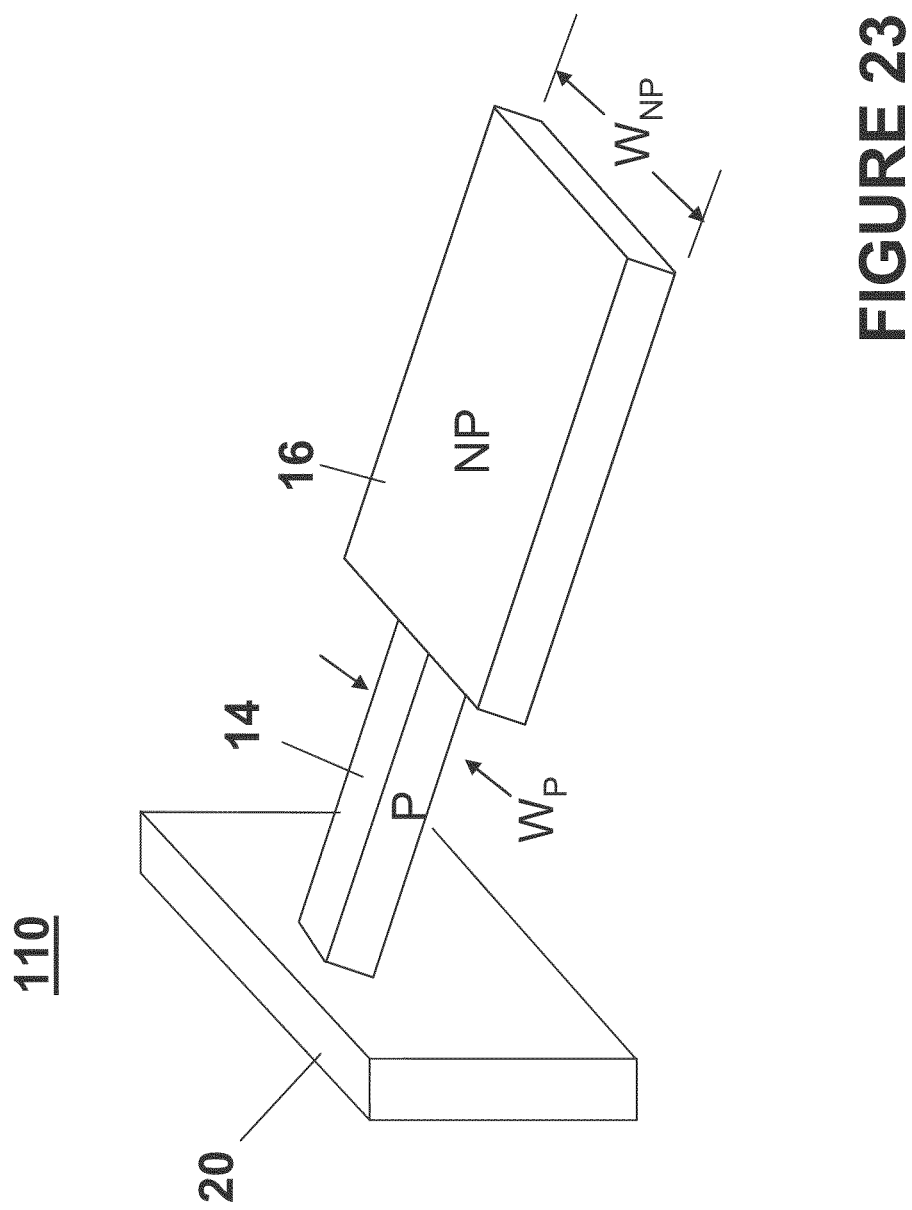
FIG. 23 is an illustration of an example configuration of an unanchored piezoelectric cantilever sensor comprising a piezoelectric portion and a non-piezoelectric portion, wherein the width of the piezoelectric portion is less than the width of the non-piezoelectric portion.

FIG. 23 is an illustration of an example configuration 110 of an unanchored piezoelectric cantilever sensor comprising a piezoelectric portion 14 and a non-piezoelectric portion 16, wherein the width, $W_P$, of the piezoelectric portion is less than the width, $W_{NP}$, of the non-piezoelectric portion 16. The configuration 110 depicted in FIG. 23 is similar to the configuration 12 depicted in FIG. 17, with the exception that $W_P$ is less than $W_{NP}$. According, the piezoelectric cantilever sensor 110 depicts an embodiment of an unanchored, overhang, piezoelectric cantilever sensor. The piezoelectric portion 14 is coupled to the non-piezoelectric portion 16 via adhesive portion or the like, for example, (adhesive portion not shown in FIG. 23). The adhesive portion is positioned between the overlapping portions of the piezoelectric portion 14 and the non-piezoelectric portion 16. The piezoelectric portion 14 is coupled to a base portion 20.

Figure 24:
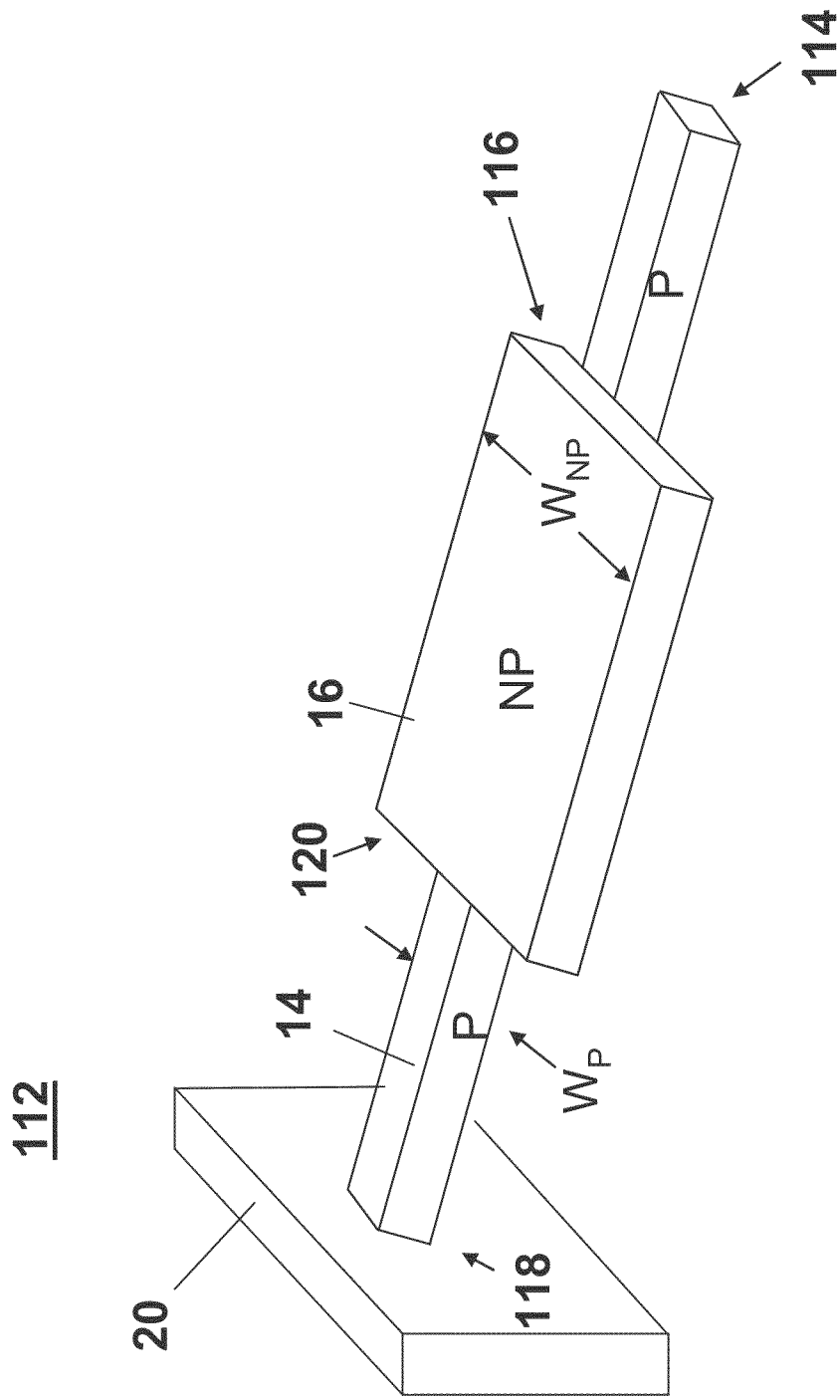
FIG. 24 is an illustration of an example configuration of an unanchored piezoelectric cantilever sensor comprising a piezoelectric portion and a non-piezoelectric portion, wherein the width of the piezoelectric portion is less than the width of the non-piezoelectric portion and wherein the distal end of the piezoelectric portion extends beyond the distal end of the non-piezoelectric portion and the proximate end of the piezoelectric portion extends beyond the proximate end of the non-piezoelectric portion.

FIG. 24 is an illustration of an example configuration 112 of an unanchored piezoelectric cantilever sensor comprising a piezoelectric portion 14 and a non-piezoelectric portion 16, wherein the width, $W_P$, of the piezoelectric portion is less than the width, $W_{NP}$, of the non-piezoelectric portion 16, and wherein the distal end 114 of the piezoelectric portion 14 extends beyond the distal end 116 of the non-piezoelectric portion 16 and the proximate end 118 of the piezoelectric portion 14 extends beyond the proximate end 120 of the non-piezoelectric portion 16. The configuration 112 depicted in FIG. 24 is similar to the configuration 42 depicted in FIG. 14, with the exception that $W_P$ is less than $W_{NP}$. The piezoelectric portion 14 is coupled to the non-piezoelectric portion 16 via adhesive portion or the like, for example, (adhesive portion not shown in FIG. 24). The adhesive portion is positioned between the overlapping portions of the piezoelectric portion 14 and the non-piezoelectric portion 16. The piezoelectric portion 14 is coupled to the base portion 20.

Figure 25:
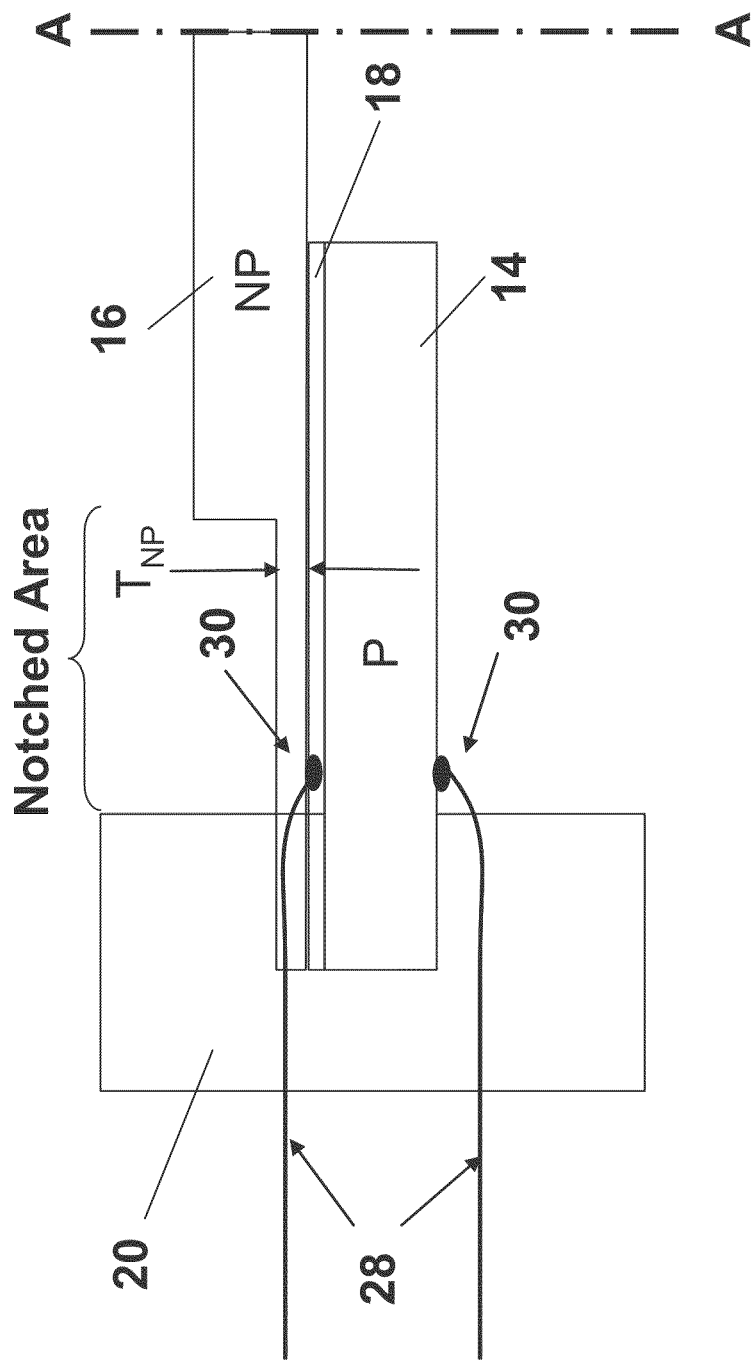
FIG. 25 depicts a configuration of a piezoelectric cantilever sensor wherein the NP section is contiguous with the P section.

FIG. 25 depicts a configuration of a piezoelectric cantilever sensor wherein the NP section 16 is contiguous with P section 14. The thickness of the NP layer 16 ($T_{NP}$) can vary along length of the NP layer 14 and $T_{NP}$ can be designed to support a sensitive sensor. In this configuration, the modulus of bending is in the NP layer 14 notched area is less than that of the thicker portion of the NP layer 14. Although only a free-end cantilever arm comprising a P and NP layer are shown, the configuration of FIG. 25 may be duplicated in mirror form about the center line A-A. This mirror duplication of FIG. 25 depicts a symmetry for a beam type piezoelectric cantilever sensor. There are several instances of a centerline depiction in FIGS. 25-36 where the geometry depiction can be either a free-end cantilever or a beam type configuration of sensor. In addition, all of the basic information about electrode wire 28 and contact 30 placement and the width of the notch applies to this configuration and to all others.

Figure 26:
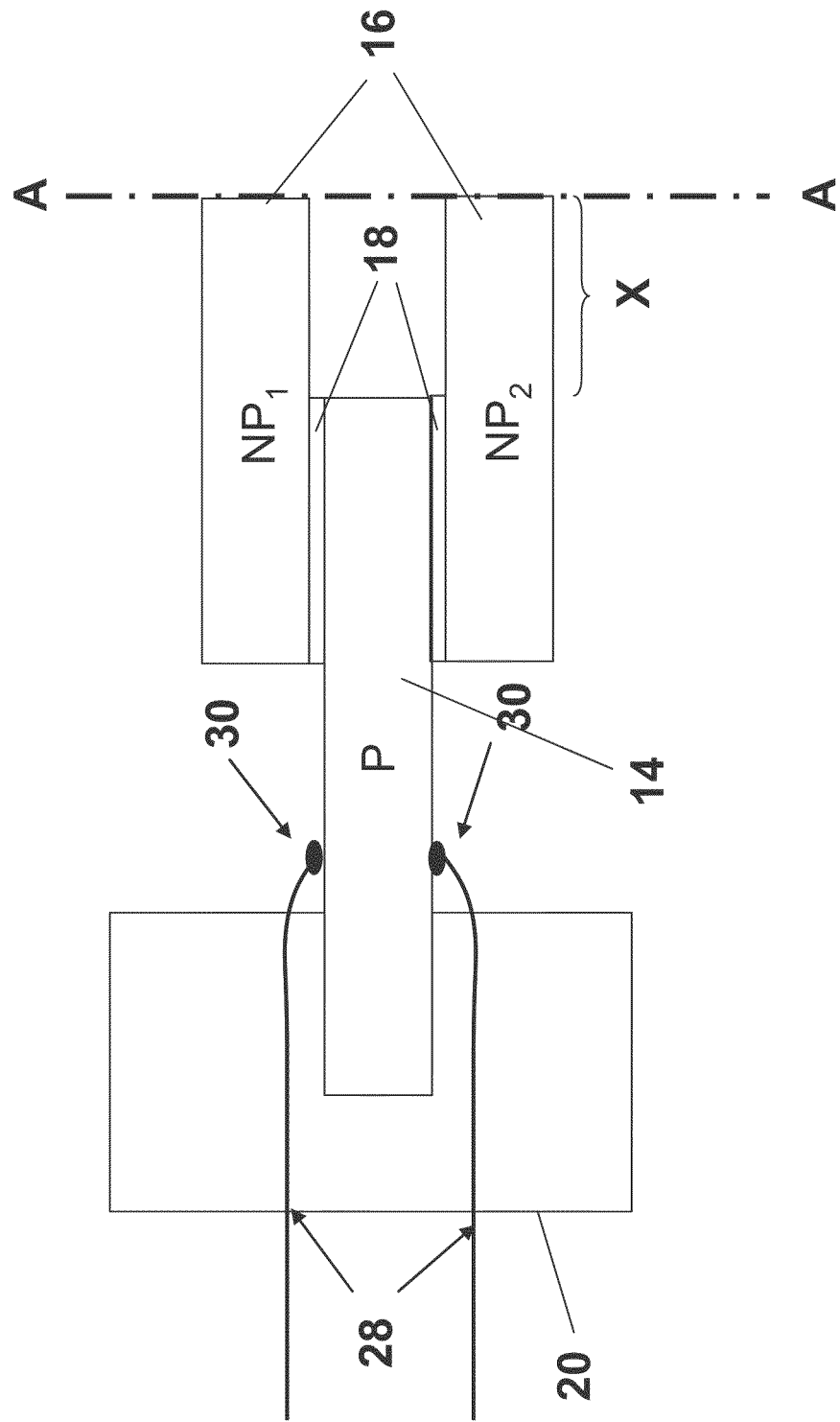
FIG. 26 depicts an example configuration of a piezoelectric cantilever sensor comprising two layers of NP.

FIG. 26 depicts two layers of NP 16; one at the top and one at the bottom, which can be used effectively if the Bending Modulus (EI) of NP1 is not equal to that of NP2 Here, the designations NP1 and NP2 on FIG. 26 indicate that the two NP layers may differ in geometry as well as material. For example, NP1 can be smaller or a different shape than NP2. Also NP1 can be made of glass whereas NP2 is made of ceramic. As in FIG. 25, the mirror image around centerline A-A would create a beam configuration. In this case, the distance X is greater than or equal to 0, meaning that P can be contiguous to the mirror anchor or it could be two separate pieces. In the case where X>0, you could excite one or BOTH pieces of P but in the later case the two excitations could be synchronized.

Figure 27:
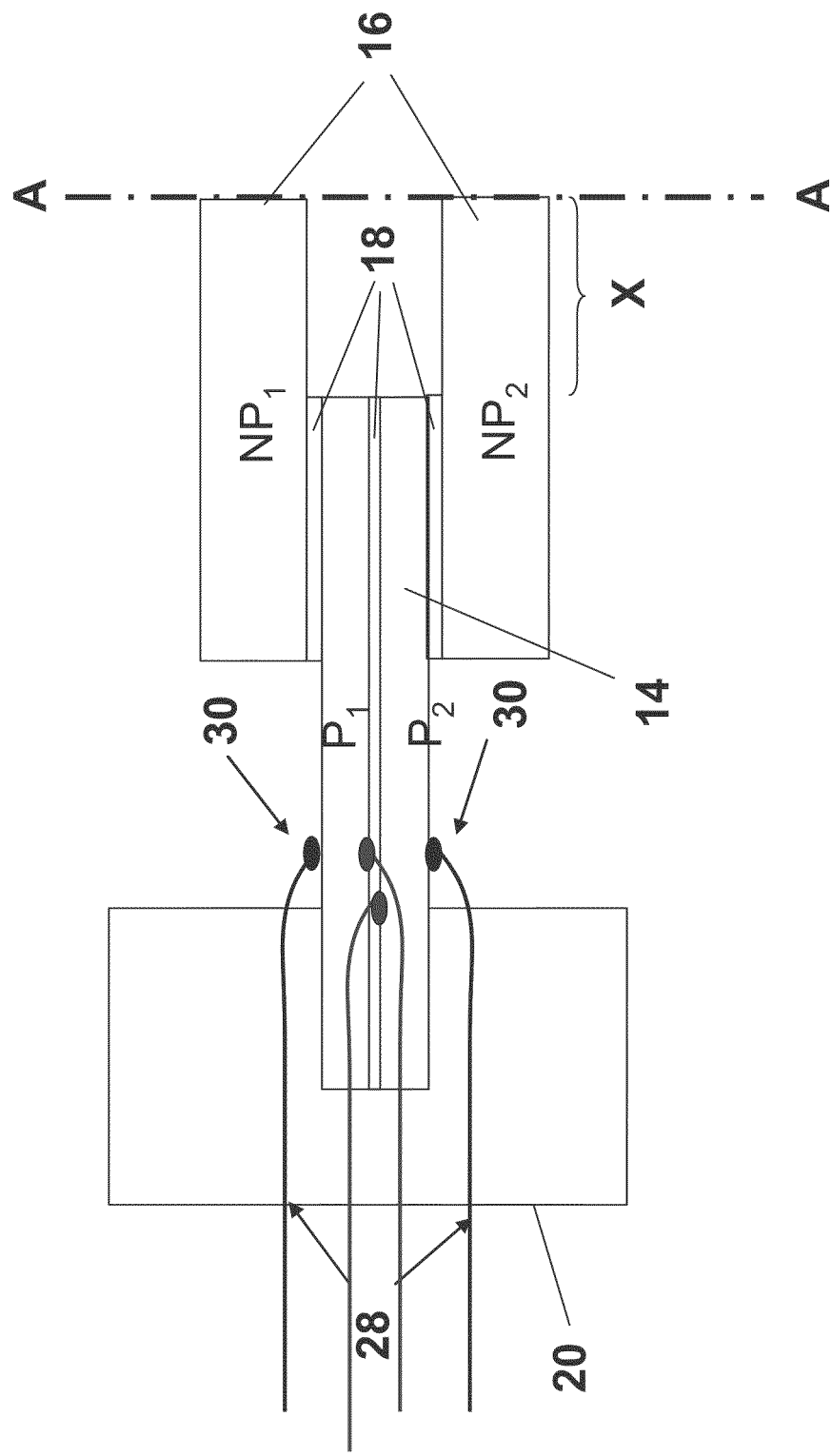
FIG. 27 depicts an example configuration of a piezoelectric cantilever sensor comprising two piezoelectric portions.

FIG. 27 depicts an example configuration of a piezoelectric cantilever sensor comprising two piezoelectric portions 18, P1 and P2. P1, P2, or both can be excited for operation.

Figure 28:
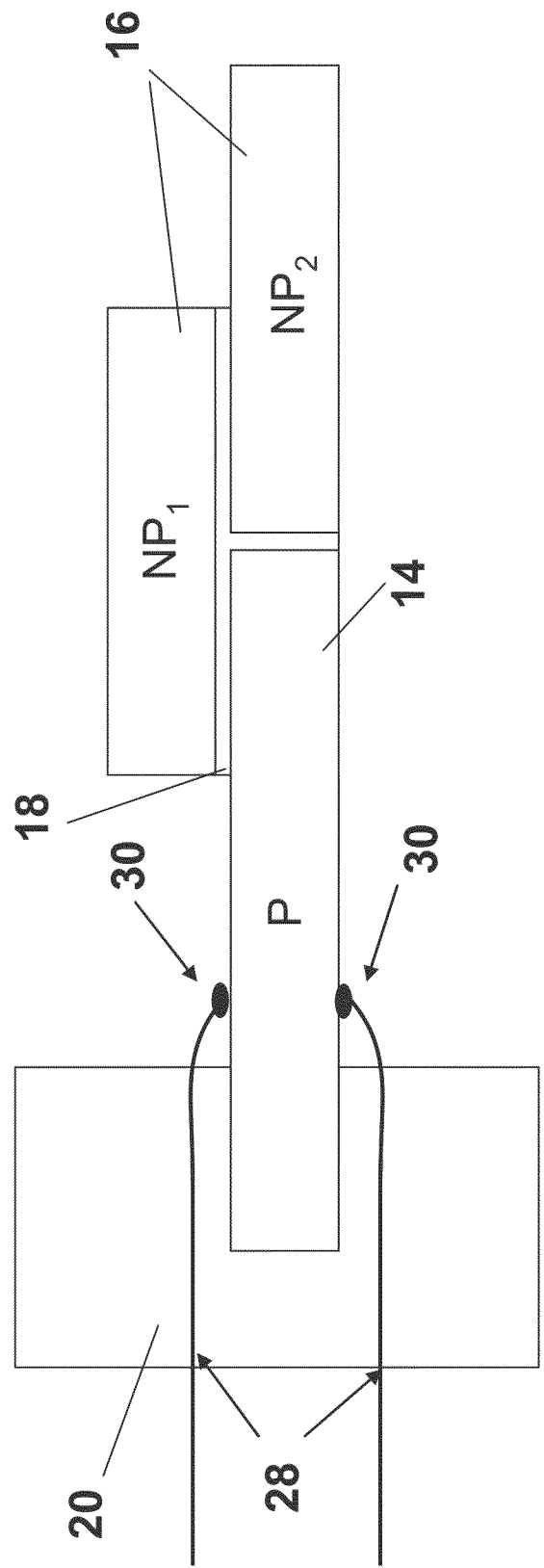
FIG. 28 depicts an example configuration of a piezoelectric cantilever sensor comprising an additional piece of NP type material.

FIG. 28 depicts an example configuration of a piezoelectric cantilever sensor comprising an additional piece of NP 16 type material. This structure provides more control over the position of the resonant frequency peak, and can be effective in dampening unwanted modes. NP1 16 can be equal or unequal to NP2 16 depending on the desired properties.

Figure 29:
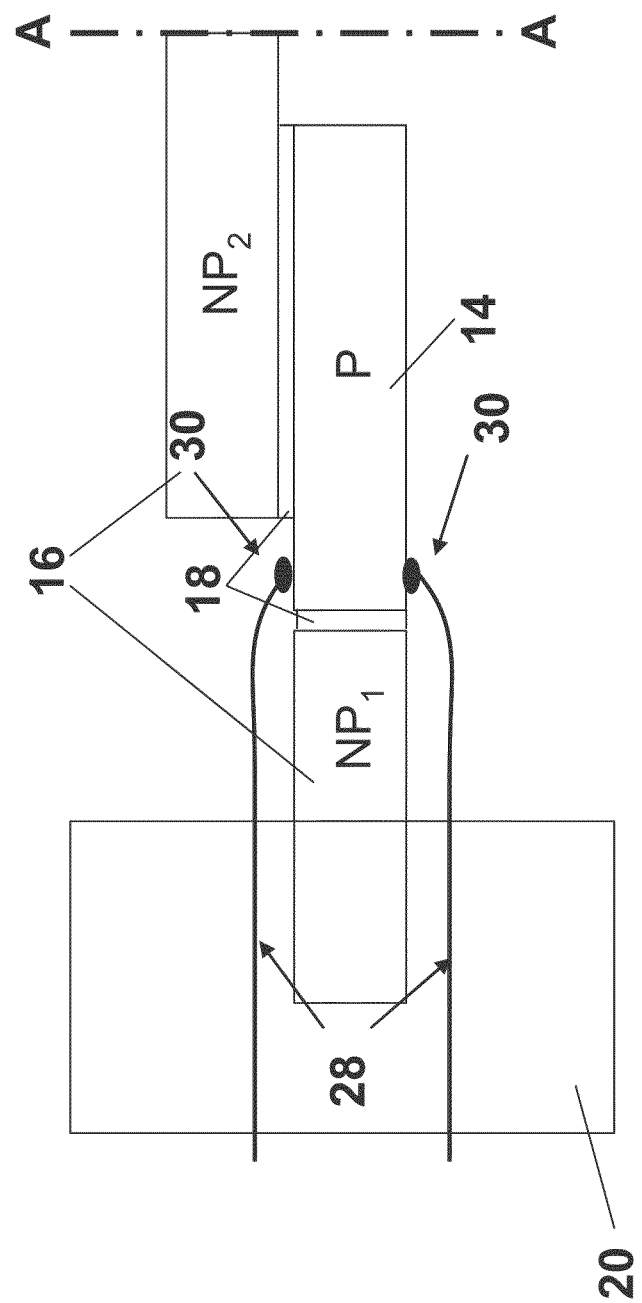
FIG. 29 depicts another example configuration of a piezoelectric cantilever sensor comprising an addition of NP1.

FIG. 29 depicts another example configuration of a piezoelectric cantilever sensor comprising an addition of NP1. Here, NP1 connects to base 20 instead of a P type of layer. This configuration can offer an enhanced signal because the proximal end of P is not constrained so that some of its signal energy is not dissipated, thereby generating a larger signal.

Figure 30:
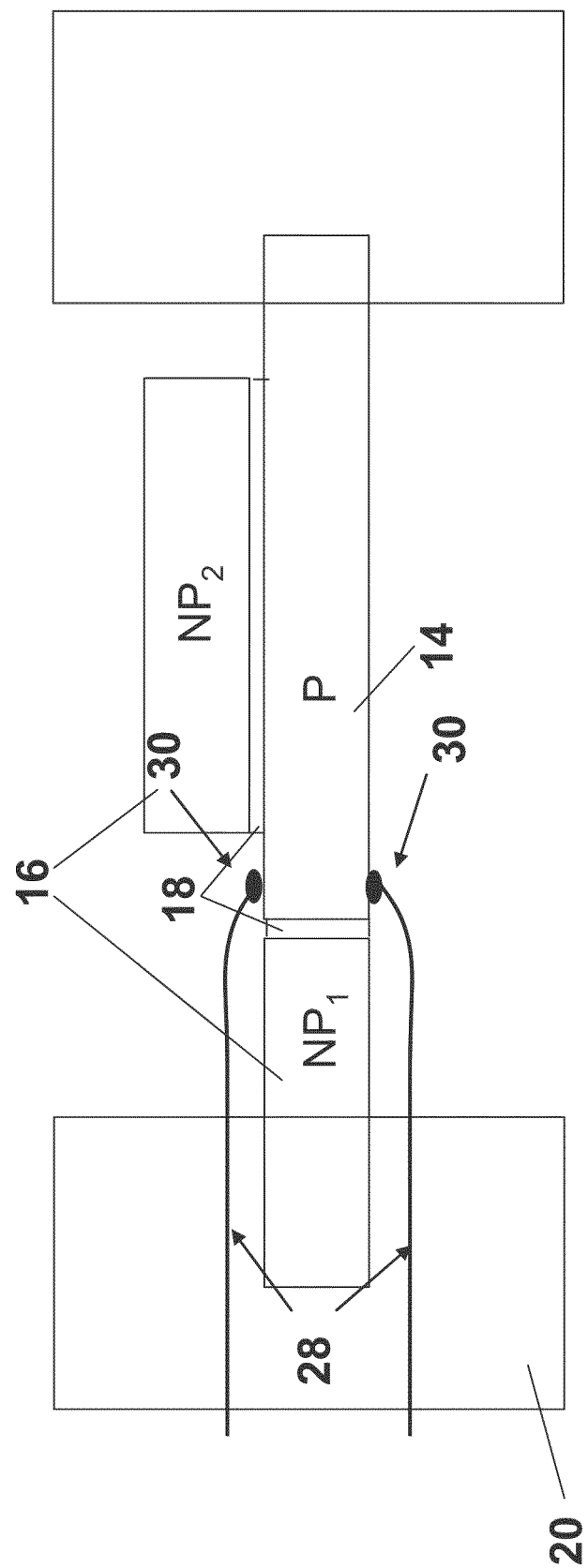
FIG. 30 depicts an example configuration of a piezoelectric cantilever sensor comprising a reversal of the P and NP regions.

FIG. 30 depicts an example configuration of a piezoelectric cantilever sensor comprising a reversal of the P and NP regions and the addition of the P type of layer 14, as compared to the configuration of FIG. 29. This configuration may offer an enhanced signal because the proximal end of NP2 is not constrained such some of its signal energy may not be dissipated.

Figure 31:
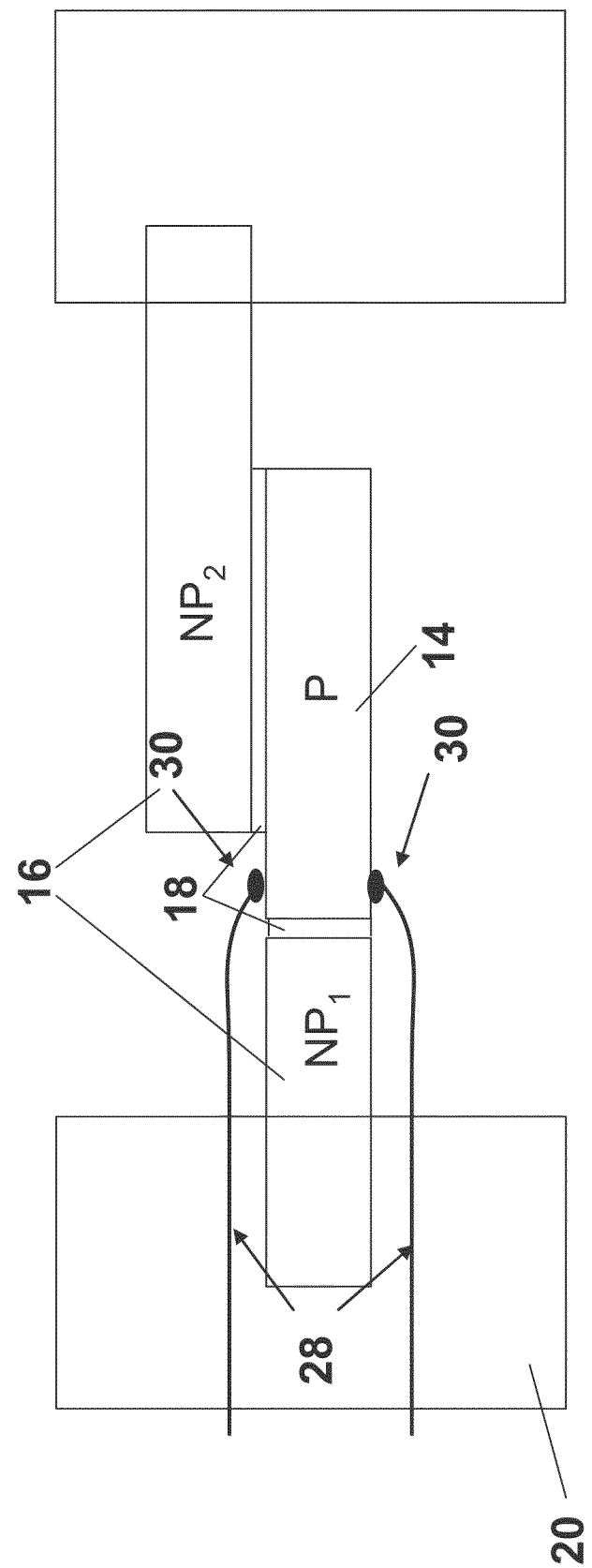
FIG. 31 depicts another example configuration of a piezoelectric cantilever sensor comprising an addition of NP1.

FIG. 31 depicts an example configuration of a piezoelectric cantilever sensor comprising an addition of NP1. This configuration may offer an enhanced signal because the proximal end of P is not constrained such that some of its signal energy may not be dissipated.

Figure 32:
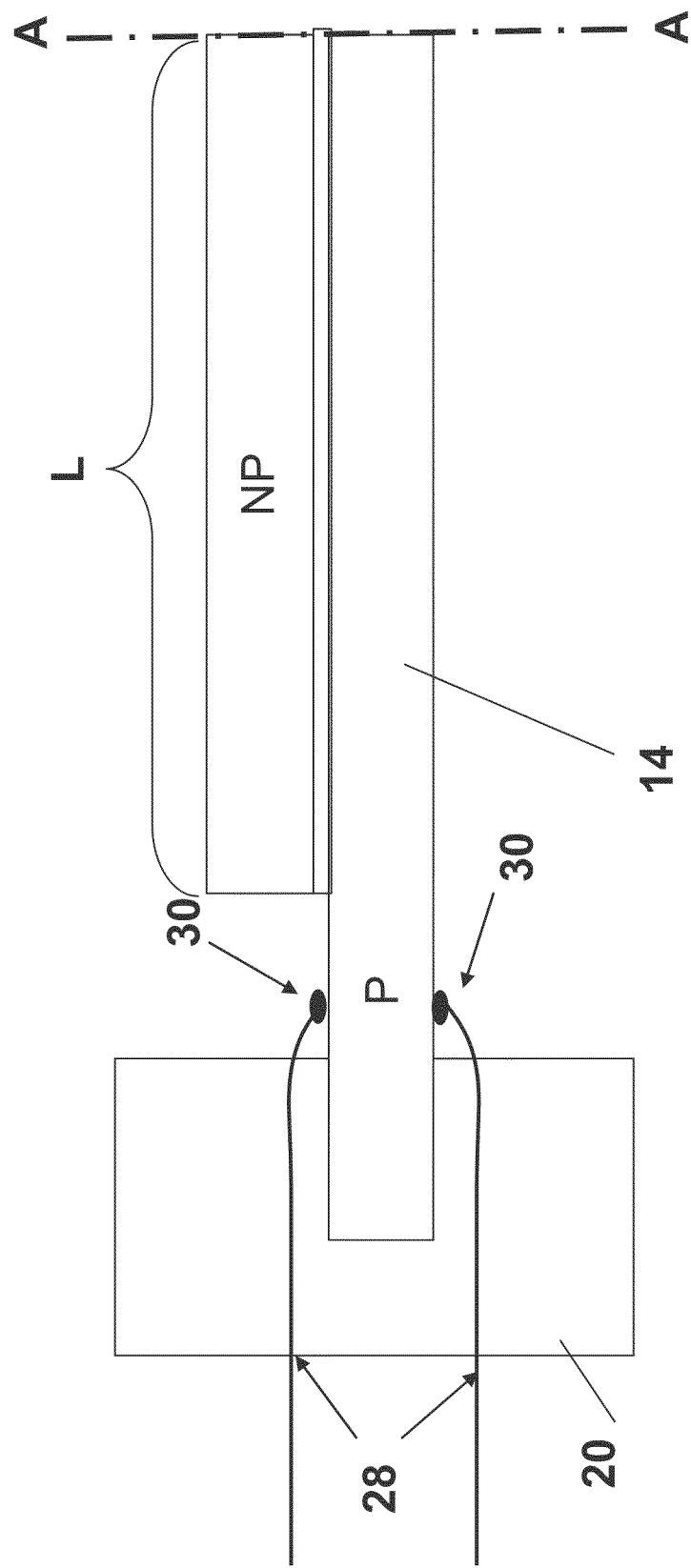
FIG. 32 depicts an example configuration of a piezoelectric cantilever sensor similar wherein the Bending Modulus of the NP layer varies as a function of the length L.
Figure 33:
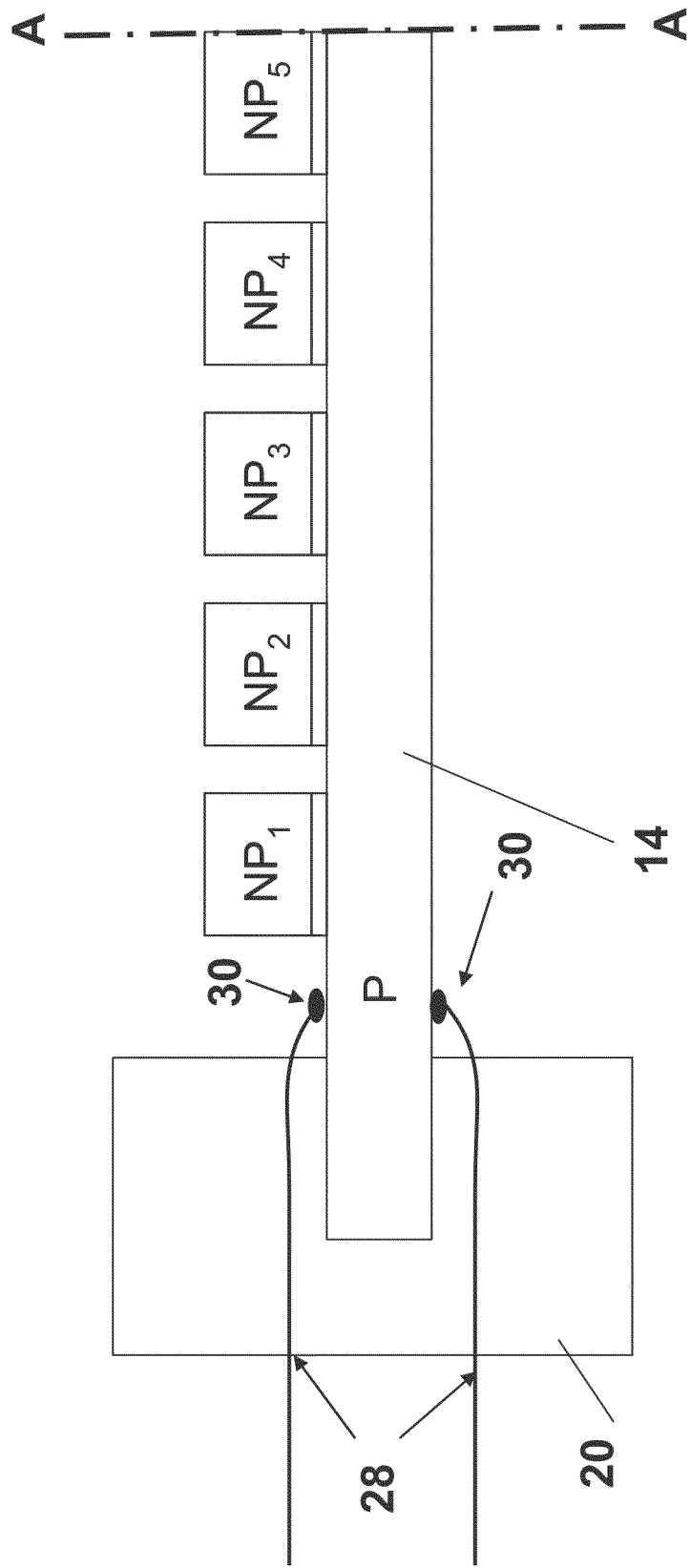
FIG. 33 depicts an example configuration of a piezoelectric cantilever sensor wherein the NP layer is composed of multiple discrete segments.

FIG. 32 depicts an example configuration of a piezoelectric cantilever sensor similar wherein the Bending Modulus (EI) of the NP layer varies as a function of the length L. By varying the parameter L, an enhancement in sensitivity by increasing the stress concentrated at the position of the electrodes is achieved. One practical way to achieve this would be as shown in FIG. 33 where the NP layer is composed of multiple discrete segments which can vary in width along with adjacent sections that are empty space or an alternate material of a lower modulus. A beam configuration is created by adding the mirror image around A-A in either of FIG. 32 or 33.

Figure 34:
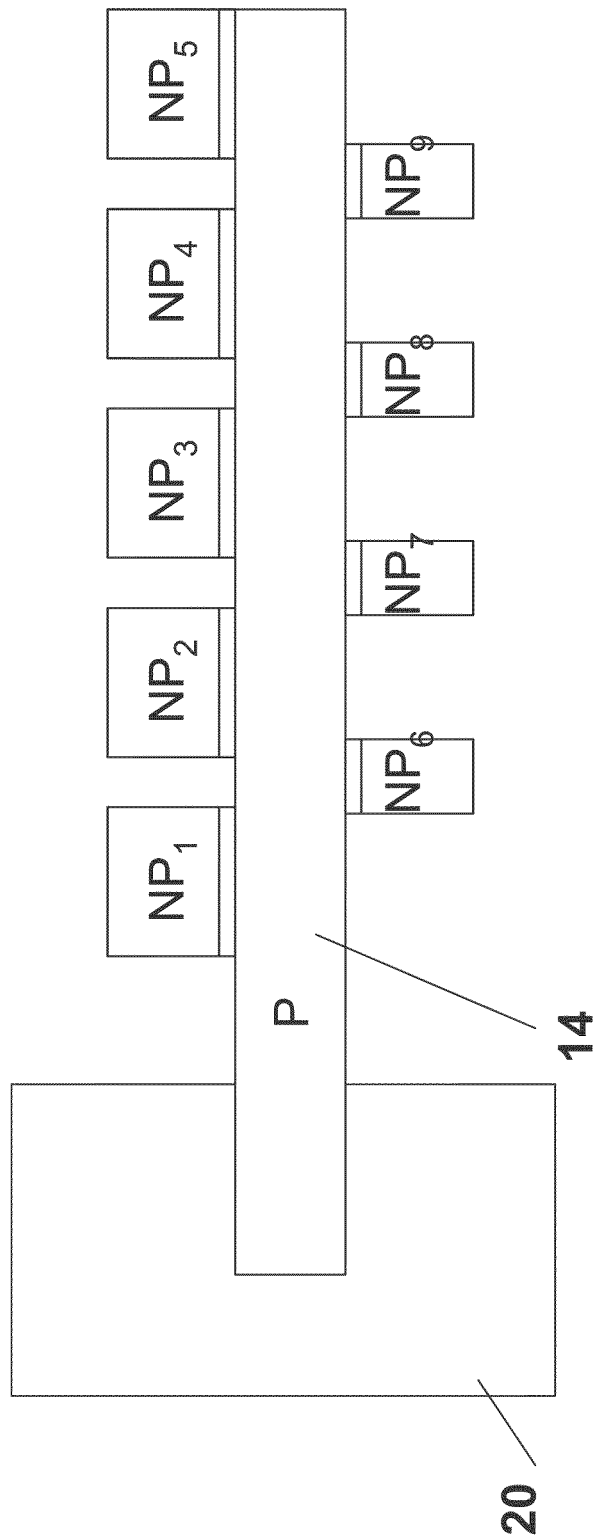
FIG. 34 depicts an example configuration of a piezoelectric cantilever sensor wherein the top NP layer has a Bending Modulus that varies as a function of length and a bottom layer that varies as a function of length.

FIG. 34 is a configuration that is similar to FIG. 26 except that the top NP layer has a Bending Modulus (EI) that varies as a function of length and a bottom layer that varies as a function of length. This is effectively the mirror image of FIG. 33 but where the bottom layer is different than the top layer to create a resonant structure.

Figure 35:
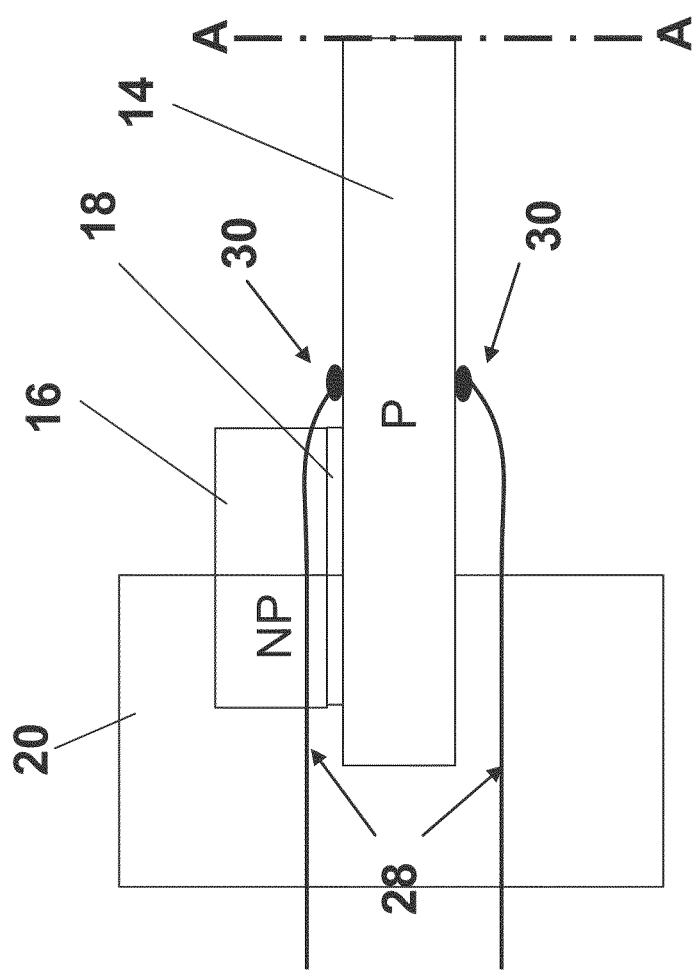
FIG. 35 depicts an example configuration of a piezoelectric cantilever sensor that concentrates stress at the point of the electrodes.
Figure 36:
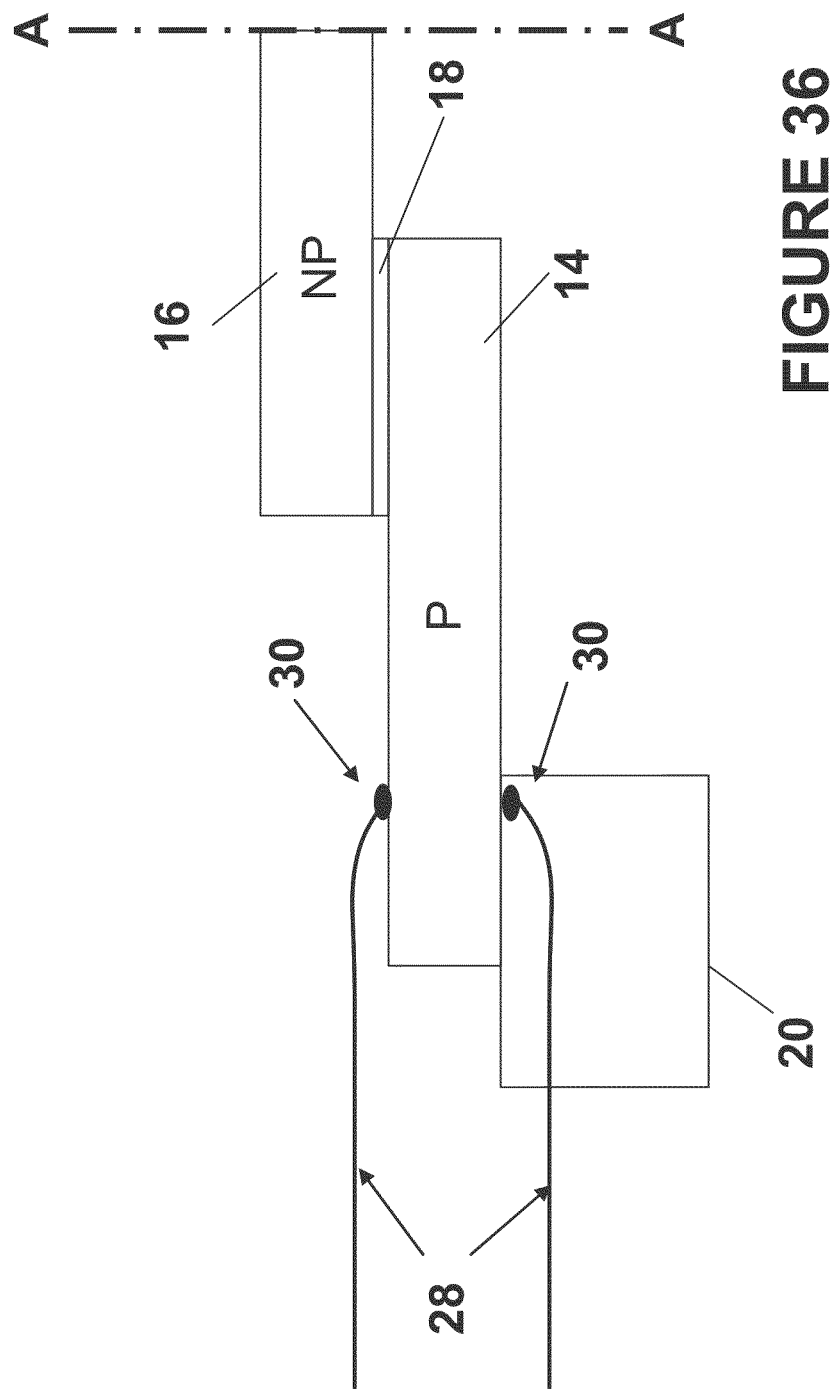
FIG. 36 depicts an example configuration of a piezoelectric cantilever sensor comprising an abbreviated base 20.

FIG. 35 is a configuration that concentrates stress sufficiently at the point of the electrodes to create a sensitive response. However, it gives a more stable response due to the position of NP 16. A beam can structure can be created by mirroring around the A-A centerline. FIG. 36 is a configuration that is useful for manufacturability because of the abbreviated base 20. However, it provides more unwanted vibration modes. A beam structure is created by mirroring about the A-A centerline.

Figure 37:
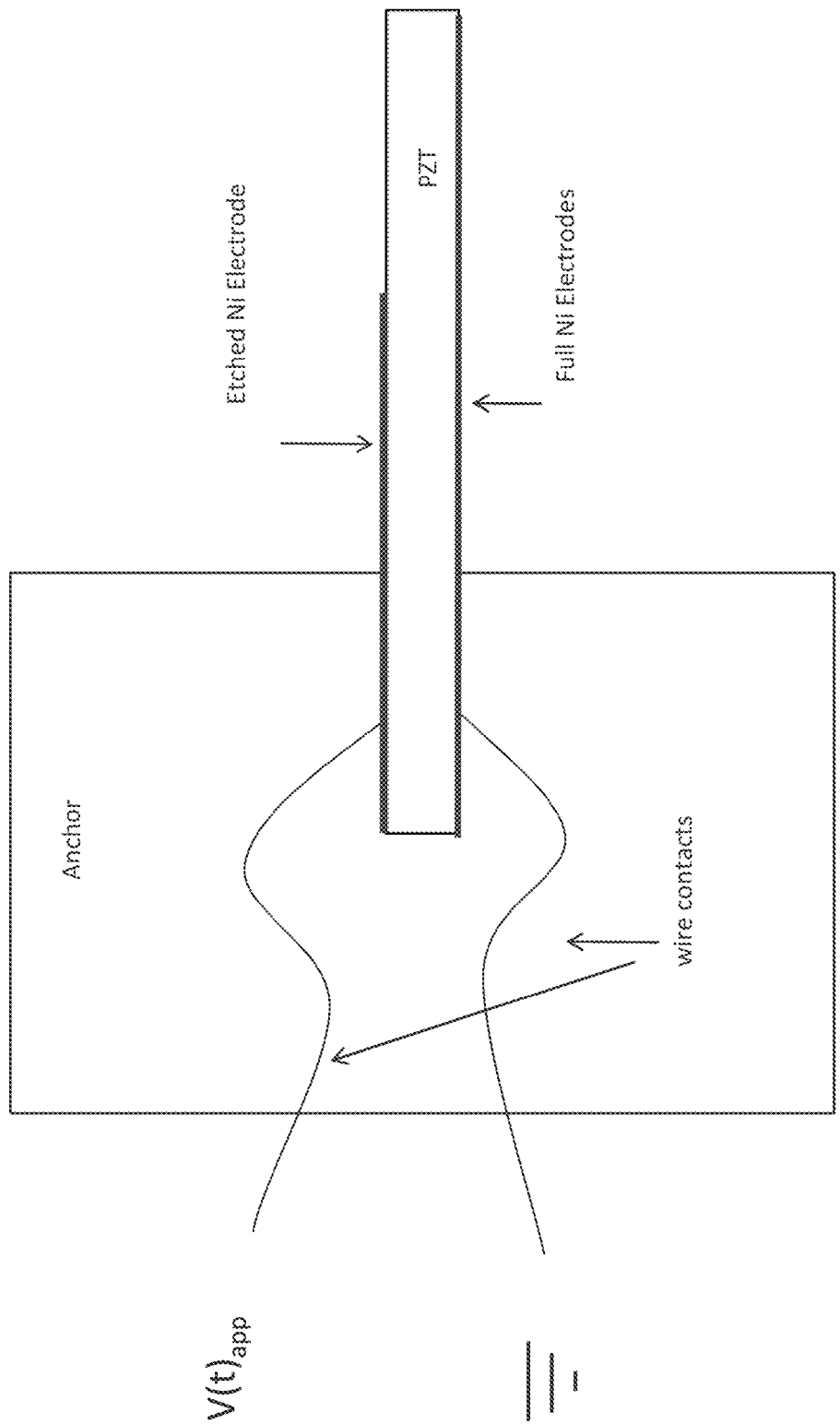
FIG. 37 depicts a cantilever sensor comprising a single PZT cantilever having a portion of an electrode removed.

FIG. 37 depicts a cantilever sensor comprising a single led zirconate titantate (PZT) cantilever having a portion of a nickel (Ni) electrode removed. A sinusoidal excitation voltage, V(t)app, applied across the Ni electrodes give rise to expression of the mechanical resonance of the cantilever sensor. The asymmetric electrode causes differential strain in the PZT cantilever and induces bending mode resonance that is measurable by a change in electrical impedance of the sensor.

Figure 38:
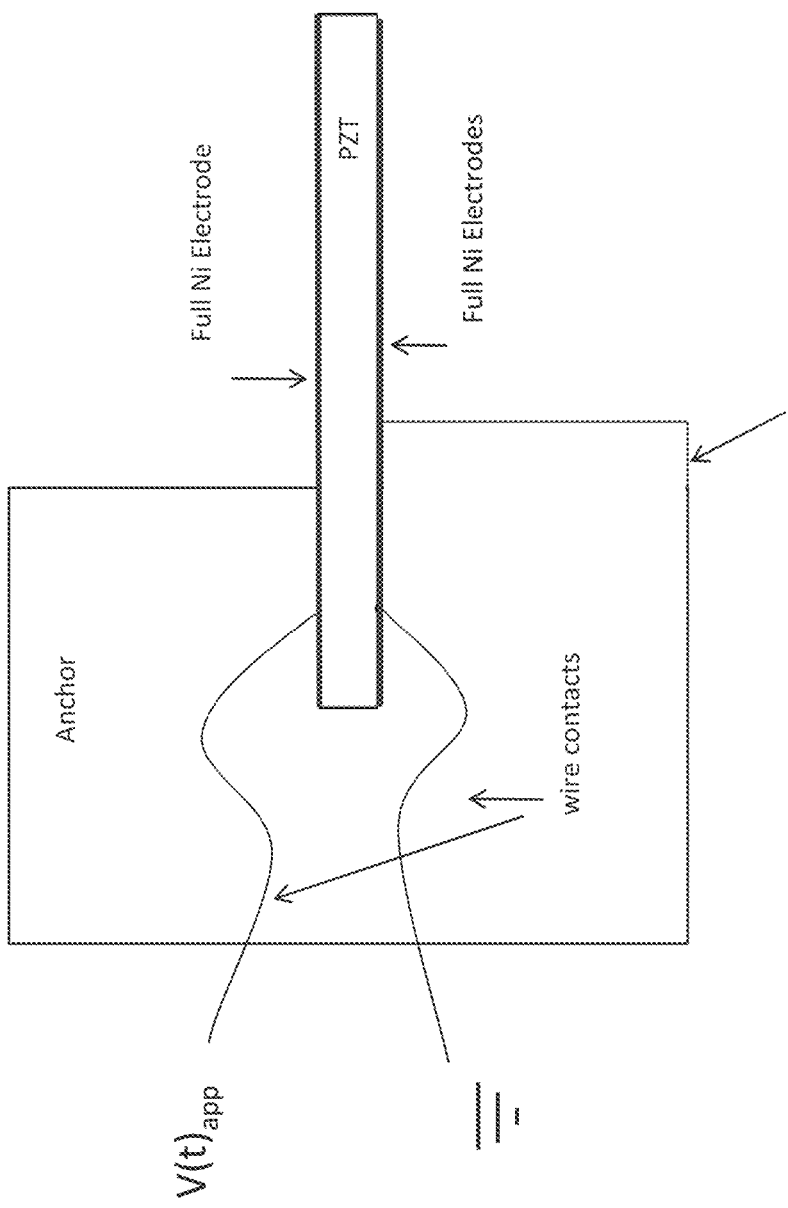
FIG. 38 depicts a cantilever sensor comprising a single PZT cantilever having an asymmetric anchor.

FIG. 38 depicts a cantilever sensor comprising a single led zirconate titantate (PZT) cantilever having an asymmetric anchor. As shown in FIG. 38, one side (the top side in FIG. 38) of the cantilever is longer than the other side (the bottom side in FIG. 38) of the cantilever. The sensor depicted in FIG. 38 exhibits resonance behavior with Q values between 20-80 in liquids. In an example configuration, the cantilever is 1 mm width and 2 to 4 mm long. In example configurations, the difference in topside length and bottom side length can be as small as 0.1% and as large as 50% (tested to date). The asymmetric anchor causes differential strain in the PZT cantilever that induces bending mode resonance that is measurable by a change in electrical impedance of the sensor.

Figure 39:
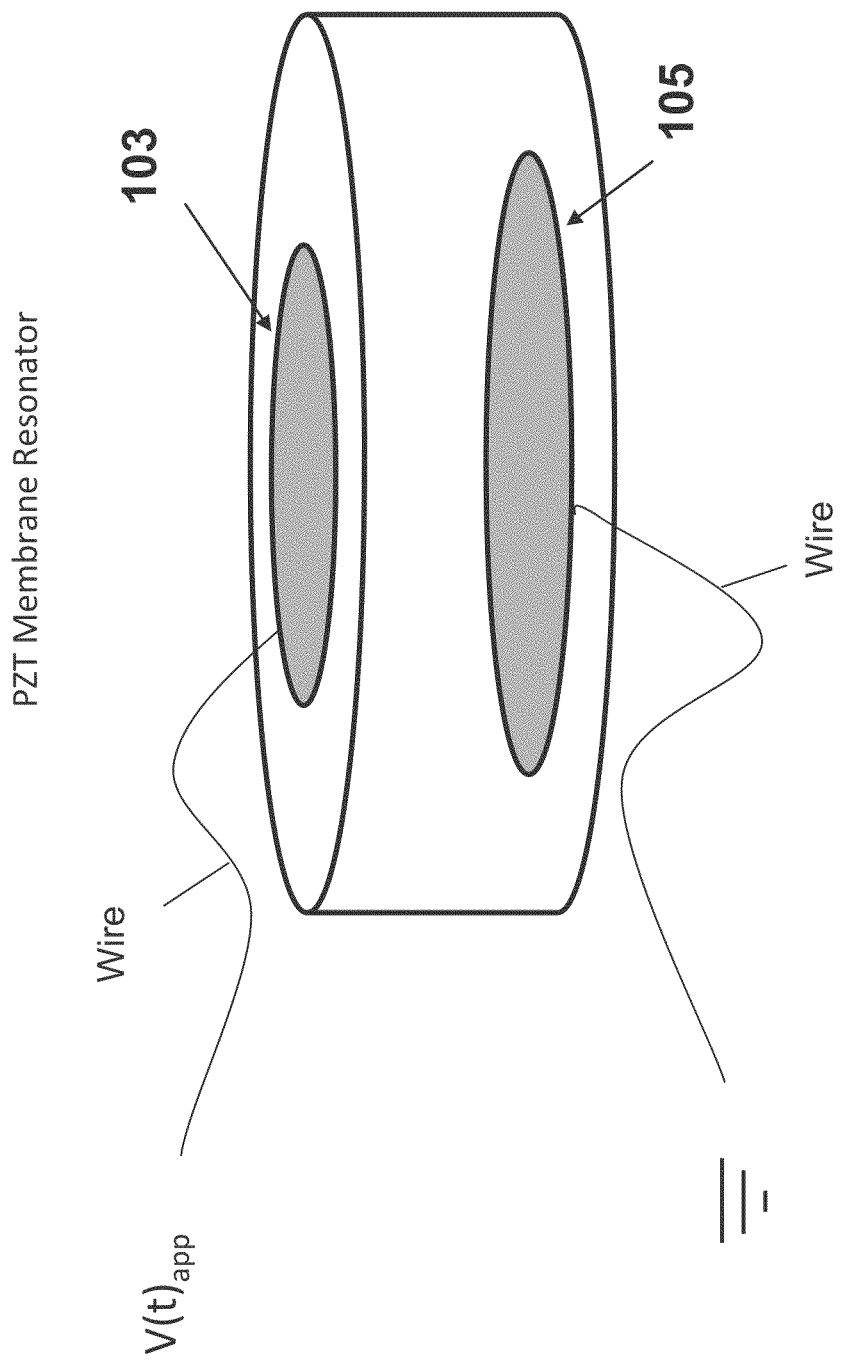
FIG. 39 is a depiction of an electromechanical resonator comprising PZT membranes.

FIG. 39 is a depiction of an electromechanical resonator comprising led zirconate titantate (PZT) membranes with electrodes 103 and 105. The electromechanical resonator depicted in FIG. 39 is a PZT membrane resonator with the circumference anchored appropriately. The electrodes 103, 105, can be any appropriate shape. For example, the membranes 103, 105 can be rectangular, circular, oval, square, of an polygonal shape. As depicted in FIG. 39, the membranes 103, 105 are circular shaped. In an example configuration, as depicted in FIG. 39, the electrodes 103, 105 are of different areas introducing asymmetric exciation of the PZT layer causing asymmetric strain in PZT. The resonator depicted in FIG. 39 exhibits mechanical resonance that is measurable by a change in impedance of the sensor.

Figure 40:
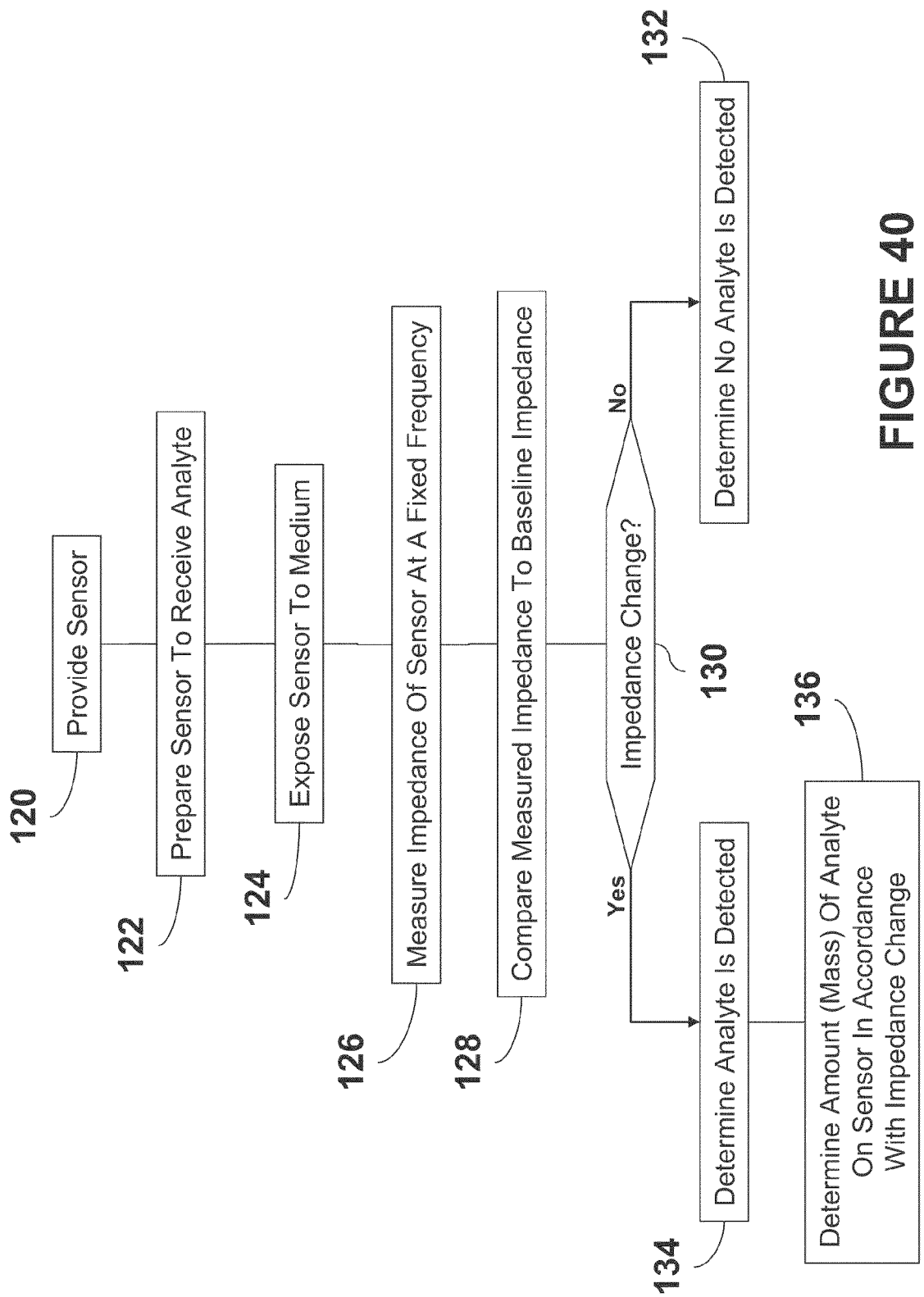
FIG. 40 is a flow diagram of an example process for detecting an analyte utilizing impedance determinations.

FIG. 40 is a flow diagram of an example process for detecting an analyte utilizing the herein described impedance approach. A sensor is provided at step 120. Any appropriate sensor can be provided. For example, an electromechanical resonating sensor can be provided, a QCM sensor can be provided, a piezoelectric cantilever sensor can be provided, or the like. The sensor can be configured as a piezoelectric cantilever sensor in accordance with the descriptions provided above, or configured in accordance with any appropriate variant thereof. The sensor is prepared to receive an analyte at step 122. In an example embodiment, an analyte attractor is applied to a portion of the sensor. In an example embodiment, an analyte attractor is applied to the non-piezoelectric portion of a piezoelectric cantilever sensor. The attractor is specific to an analyte. Thus the attractor will attract a target analyte and not attract other substances. For example, the sensor (e.g., a non-piezoelectric portion of a piezoelectric cantilever sensor) can comprise an attractor for attracting bioterrorism agents, such as *Bacillus anthracis*, food-borne pathogens, such as *E. coli*, pathogens in food and water, cell types in body fluids (e.g., circulating tumor cells), biomarkers in body fluids (e.g., proteins that mark specific pathophysiology-alpha-fetoprotein, beta-2-microglobulin, bladder tumor antigen, breast cancer marker CA-15-3, and other CAs (cancer antigens), calcitonin, carcinoembryonic antigen, and others), markers of explosives such as trinitrotoluene, dinitrotoluene, airborne and waterborne toxins, biological entities, such as a protein, or a combination thereof, for example.

The sensor is exposed to a medium at step 124. The medium can comprise any appropriate medium, such as a liquid, a gas, a combination of a liquid and a gas, or a vacuum, for example. The medium can exhibit a wide variety of flow conditions. If a target analyte is present in the medium, the target analyte will accumulate on the portion of the sensor that has been treated with the attractor. As described above, when the sensor is a piezoelectric cantilever sensor, accumulation (e.g., binding) of the target analyte on the non-piezoelectric portion of the piezoelectric cantilever sensor will result in a change in stiffness of the piezoelectric cantilever sensor and/or an increase the mass of the piezoelectric cantilever sensor, which will decrease the resonance frequency of the piezoelectric cantilever sensor, and will change the impedance of the piezoelectric cantilever sensor.

The impedance of the sensor is measure at step 126. The impedance can be measured by at any appropriate frequency. For example, the frequency can be a resonance frequency, ($f_R$), of the sensor, the frequency can be other than a resonance frequency of the sensor, the frequency can be a frequency with a predetermined tolerance (e.g., +/−1 kHz) of the resonance frequency of the sensor. The resonance frequency of the sensor can be a baseline resonance frequency determined prior to exposure of the sensor (step 124), the resonance frequency can be a calculated or predicted resonance frequency of the sensor with or without analyte accumulation on the sensor, or the like.

In an example embodiment, the impedance of the piezoelectric cantilever sensor is measured at a fixed frequency other than the resonance frequency and within +/−1 kHz of the predicted resonance frequency of the sensor. In an example embodiment, impedance is calculated from the vectorial ratio of the exciation voltage and the resulting current through the piezoelectric layer of a piezoelectric cantilever sensor. When the piezoelectric material of the piezoelectric portion of the piezoelectric cantilever sensor is excited, the non-piezoelectric portion of the piezoelectric cantilever sensor flexes to accommodate the strain caused in the piezoelectric material. When the frequency of excitation is the same as the natural frequency of the underlying mechanical structure, resonance occurs.

The measured impedance is compared to a baseline impedance at step 128. In an example embodiment, the baseline impedance is the value impedance measured, predicted, or the like, at the initial resonance frequency prior to a sensing step 126. The baseline impedance is the impedance of the sensor having no analyte accumulated thereon. If a difference in impedance (impedance change) between the measured impedance and the baseline impedance is not measured (at step 130), it is determined, at step 132, that no analyte is detected. If a difference in impedance between the measured impedance and the baseline impedance is measured (at step 130), it is determined, at step 134, that an analyte is detected, i.e., an analyte is present in the medium. At step 136, the amount of mass of the analyte that has accumulated on the sensor is determined in accordance with the impedance change measured at step 130. As described above, the impedance change is proportional to the change in mass of the analyte.

It is to be understood that even though numerous characteristics and advantages of detection/measurement of mass change using impedance determinations have been set forth in the foregoing description, together with details of the structure and function, the disclosure is illustrative only, and changes may be made in detail, especially in matters of shape, size, and arrangement of parts within the principles of detection and measurement of mass change using impedance determinations to the full extent indicated by the broad general meaning of the terms in which the appended claims are expressed.

While example embodiments of detection and measurement of mass change using a piezoelectric cantilever sensor have been described in connection with various computing devices/processors, the underlying concepts can be applied to any computing device, processor, or system capable of detection and measurement of mass change using a piezoelectric cantilever sensor. The various techniques described herein can be implemented in connection with hardware or software or, where appropriate, with a combination of both. Thus, the methods and apparatuses for detection and measurement of mass change using impedance determinations can be implemented, or certain aspects or portions thereof, can take the form of program code (i.e., instructions) embodied in tangible storage media. Examples of tangible storage media include floppy diskettes, CD-ROMs, DVDs, hard drives. When the program code is loaded into and executed by a machine, such as a computer, the machine becomes an apparatus for detection and measurement of mass change using impedance determinations. In the case of program code execution on programmable computers, the computing device will generally include a processor, a storage medium readable by the processor (including volatile and non-volatile memory and/or storage elements), at least one input device, and at least one output device. The program(s) can be implemented in assembly or machine language, if desired. The language can be a compiled or interpreted language, and combined with hardware implementations. As evident from the herein description, a tangible storage medium is not to be construed as a signal.

The methods and apparatuses for detection and measurement of mass change using impedance determinations also can be practiced via communications embodied in the form of program code that is transmitted over some transmission medium, such as over electrical wiring or cabling, through fiber optics, or via any other form of transmission, wherein, when the program code is received and loaded into and executed by a machine, such as an EPROM, a gate array, a programmable logic device (PLD), a client computer, or the like, the machine becomes an apparatus for detection and measurement of mass change using impedance determinations. When implemented on a general-purpose processor, the program code combines with the processor to provide a unique apparatus that operates to detect and/or measure mass change using impedance determinations.

While detection and measurement of mass change using impedance determinations have been described in connection with the various embodiments of the various figures, it is to be understood that other similar embodiments can be used or modifications and additions can be made to the described embodiments for detection and measurement of mass change using impedance determinations without deviating therefrom. Therefore, detection and measurement of mass change using impedance determinations should not be limited to any single embodiment, but rather should be construed in breadth and scope in accordance with the appended claims.

What is claimed:

1. A method comprising:
    exposing at least a portion of an electromechanical resonating sensor to a medium, wherein the sensor comprises an asymmetric anchor;
    measuring an impedance of the sensor;
    comparing the measured impedance with a baseline impedance of the sensor; and
    when the measured impedance differs from the baseline impedance, determining that an analyte is present in the medium.

2. The method of claim 1, wherein the baseline impedance is an impedance of the sensor having no analyte accumulated thereon.

3. The method of claim 1, wherein the impedance is measured at a constant frequency.

4. The method of claim 1, wherein the impedance is measured at a constant frequency other than a resonance frequency of the sensor.

5. The method of claim 1, wherein the sensor is a piezoelectric cantilever sensor comprising:
    a non-piezoelectric layer;
    a piezoelectric layer;
    at least one base portion coupled to at least one of the piezoelectric layer and the non-piezoelectric layer, wherein the at least one base portion comprises the asymmetric anchor; and
    electrodes operatively associated with the piezoelectric layer, wherein:
    at least a portion of the piezoelectric layer is coupled to at least a portion of the non-piezoelectric layer such that the piezoelectric layer and the non-piezoelectric layer are not coextensive; and
    the base portion is not attached to the proximate end of the non-piezoelectric layer.

6. The method of claim 5, wherein a difference in the measured impedance and the baseline impedance is indicative of a stress in the piezoelectric layer.

7. The method of claim 1, wherein the sensor is a quartz crystal microbalance sensor.

8. The method of claim 1, wherein the medium comprises one of a liquid, a gas, and a vacuum.

9. The method of claim 1, further comprising determining an amount of analyte accumulated on the sensor in accordance with the difference between the measured impedance and the baseline impedance.

10. The method of claim 1, wherein the analyte comprises at least one of a bioterrorism agent, a food-borne pathogen, a water pathogen, a cell type in a body fluids, a biomarker in a body fluid, an indication of an explosive material, an airborne toxin, a waterborne toxin, and a biological entity.

11. The method of claim 1, further comprising determining a change in an amount of mass of an analyte accumulated on the sensor in accordance with the difference between the measured impedance and the baseline impedance, wherein the change in an amount of mass of the analyte is proportional the difference between the measured impedance and the baseline impedance.

12. The method of claim 1, wherein the sensor is a piezoelectric cantilever sensor comprising:
    a non-piezoelectric layer;
    a piezoelectric layer;
    a first base portion comprising a first portion of the asymmetric anchor coupled to one of the piezoelectric layer and the non-piezoelectric layer;
    a second base portion comprising a second portion of the asymmetric anchor coupled to one of the piezoelectric layer and the non-piezoelectric layer; and
    electrodes operatively associated with the piezoelectric layer, wherein at least a portion of the piezoelectric layer is coupled to at least a portion of the non-piezoelectric layer such that the piezoelectric layer and the non-piezoelectric layer are not coextensive.

* * * * *